(12) United States Patent
Hochstrasser et al.

(10) Patent No.: US 9,028,825 B2
(45) Date of Patent: May 12, 2015

(54) DIAGNOSTIC METHOD FOR BRAIN DAMAGE-RELATED DISORDERS

(75) Inventors: Denis Francois Hochstrasser, Geneva (CH); Jean-Charles Sanchez, Geneva (CH)

(73) Assignee: Universite de Geneve, Geneva (CH)

( * ) Notice: Subject to any disclaimer, the term of this patent is extended or adjusted under 35 U.S.C. 154(b) by 1104 days.

(21) Appl. No.: 11/995,501

(22) PCT Filed: Jul. 14, 2006

(86) PCT No.: PCT/GB2006/050207
§ 371 (c)(1),
(2), (4) Date: Jan. 11, 2008

(87) PCT Pub. No.: WO2007/007129
PCT Pub. Date: Jan. 18, 2007

(65) Prior Publication Data
US 2008/0220013 A1 Sep. 11, 2008

(30) Foreign Application Priority Data
Jul. 14, 2005 (GB) .................................. 0514435.7

(51) Int. Cl.
*A61K 39/395* (2006.01)
*C07K 16/40* (2006.01)
*G01N 33/68* (2006.01)

(52) U.S. Cl.
CPC ........ *G01N 33/6896* (2013.01); *G01N 33/6893* (2013.01); *G01N 2800/28* (2013.01); *G01N 2800/30* (2013.01)

(58) Field of Classification Search
None
See application file for complete search history.

(56) References Cited

U.S. PATENT DOCUMENTS

| 2003/0054415 A1 | 3/2003 | Buhring et al. |
| 2003/0109002 A1 | 6/2003 | Ullrich et al. |
| 2005/0255484 A1 | 11/2005 | Valkirs et al. |

FOREIGN PATENT DOCUMENTS

| WO | WO 97/48723 | 12/1997 | |
| WO | WO 01/42793 | 6/2001 | |
| WO | 0167108 | 9/2001 | |
| WO | WO 2004/040316 | 5/2004 | |
| WO | WO 2005/029088 | 3/2005 | |
| WO | WO 2005029088 A2 * | 3/2005 | ............. C07K 14/02 |
| WO | WO 2006/021810 | 3/2006 | |
| WO | WO 2006/035237 | 4/2006 | |
| WO | 2006061609 A2 | 6/2006 | |
| WO | WO 2006/061610 | 6/2006 | |

OTHER PUBLICATIONS

Zimmerman-Ivol et al., Molecular and Cellular Proteomics, 3(1): 66-72, 2004.*
You et al., Proteomics, 5:290-296, Jan. 2005.*
Wylie-Modro et al., Pediatric Research, 42(2):232-236, Aug. 1997.*
Wylie-Modro et al., Pediatric Research, 42:232-236, 1997.*
Chen et al., PNAS, 101[49]:17039-17044, 2004.*
Manevich et al., PNAS, 101(11):3780-3785, 2004.*
Susan Adams et al., "Signal-Regulatory Protein is Selectively Expressed by Myeloid and Neuronal Cells," The Journal of Immunology, vol. 161, pp. 1853-1859 (1998).
Ron D. Appel et al., "Melanie II—A Third-Generation Software Package for Analysis of Two-Dimensional Electrophoresis Images: I. Features and User Interface," Electrophoresis, vol. 18, No. 15, pp. 2724-2734 (Dec. 1997).
Andreas Bitsch et al., "Serum Tau Protein Level as a Maker of Axcinal Damage in Acute Ischemic Stroke," European Neurology, vol. 47, pp. 45-51 (2002).
R.T. Cunningham et al., "Serum Neurone Specific Enolase (NSE) Levels as an Indicator of Neuronal Damage in Patients with Cerebral Infarction," European Journal of Clinical Investigation, vol. 21, Issue 5, pp. 497-500 (Oct. 1991).
Pia Davidsson et al., "Proteome Studies of Human Cerebrospinal Fluid and Brain Tissue Using a Preparative Two-Dimensional Electrophoresis Approach Prior to Mass Spectrometry," Proteomics, vol. 1, No. 3, pp. 444-452 (Mar. 2001).
Debora Dumont et al., "Proteomic Analysis of Cerebrospinal Fluid from Multiple Sclerosis Patients," Proteomics, vol. 4, No. 7, pp. 2117-2124 (Jul. 2004).
Erin J. Finehout et al., "Towards Two-Dimensional Electrophoresis Mapping of the Cerebrospinal Fluid Proteome from a Single Individual," Electrophoresis, vol. 25, No. 15, pp. 2564-2575 (Aug. 2004).
J. Matias-Guiu et al., "Myelin Basic Protein and Creatine Kinase BB Isoenzyme as CSF Markers of Intracranial Tumors and Stroke," Acta Neurologica Scandinavica, vol. 73, No. 5, pp. 461-465 (May 1986).
Manfred Heller et al., "Two-Stage Off-Gel Isoelectric Focusing: Protein Followed by Peptide Fractionation and Application to Proteome Analysis of Human Plasma," Electrophoresis, vol. 26, No. 6, pp. 1174-1188 (Mar. 2005).
Edwin R. Hendrickson et al., "High Sensitivity Multianalyte Immunoassay Using Covalent DNA-Labeled Antibodies and Polymerase Chain Reaction," Nucleic Acids Research, vol. 23, No. 3, pp. 522-529 (Feb. 11, 1995).
Manfred Herrmann, MD, PhD, et al., "Release of Glial Tissue-Specific Proteins After Acute Stroke, A Comparative Analysis of Serum Concentrations of Protein S-100B and Glial Fibrillary Acidic Protein," Stroke, vol. 31, pp. 2670-2677 (Nov. 2000).
Denis F. Hochstrasser et al., "Human Liver Protein Map: A Reference Database Established by Microsequencing and Gel Comparison," Electrophoresis, vol. 13, No. 12, pp. 992-1001 (Dec. 1992).

(Continued)

*Primary Examiner* — Daniel E Kolker
*Assistant Examiner* — Stacey N MacFarlane
(74) *Attorney, Agent, or Firm* — Arent Fox LLP

(57) ABSTRACT

A brain damage-related disorder is diagnosed in a subject by detecting at least one polypeptide, or a variant or mutant thereof, in a sample of body fluid taken from the subject, wherein the polypeptide is one for which the level is either increased or decreased in cerebrospinal fluid from deceased patients compared to cerebrospinal fluid from healthy donors.

8 Claims, 13 Drawing Sheets

(56) References Cited

OTHER PUBLICATIONS

Alexei Kharitonenkov et al., "A Family of Proteins That Inhibit Signalling Through Tyrosine Kinase Receptors," Nature, Vol: 386, pp. 181-186 (Mar. 13, 1997).

H. Kolsch, PhD, et al., "Polymorphisms in Glutathione S-Transferase Omega-1 and AD, Vascular Dementia, and Stroke," Neurology, vol. 63, No. 12, pp. 2255-2260 (Dec. 28, 2004).

Yair Lampl, MD, et al., "Cerebrospinal Fluid Lactate Dehydrogenase Levels in Early Stroke and Transient Ischemic Attacks," Stroke, vol. 2.1, No. 6, pp. 854-857 (Jun. 1990).

Giuseppina Maccarrone et al., "Mining the Human Cerebrospinal Fluid Proteome by Immunodepletion and Shotgun Mass Spectrometry," Electrophoresis, vol. 25, No. 14, pp. 2402-2412 (Jul. 2004).

Colin N. A. Palmer, PhD, et al., "Association of Common Variation in Glutathione S-Transferase Genes with Premature Development of Cardiovascular Disease in Patients with Systemic Sclerosis," Arthritis & Rheumatism, vol. 48, No. 3, pp. 854-855 (Mar. 2003).

Lennart Persson, MD, PhD, et al., "S-100 Protein and Neuron-Specific Enolase in Cerebrospinal Fluid and Serum: Markers of Cell Damage in Human Central Nervous System," Stroke, vol. 18, No. 5, pp. 911-918 (Sep.-Oct. 1987).

Alexandra Ros et al., "Protein Purification by Off-Gel Electrophoresis," Proteomics, vol. 2, No. 2, pp. 151-156 (Feb. 2002).

Asha Mary Samuel et al., "Serum Total Glutathione-S-Transferase in Stroke, a Preliminary Report," Clinical Chemistry and Laboratory Medicine, vol. 42, No. 8, pp. 984-986 (2004).

Jean-Charles Sanchez et al., "The Mouse SWISS-2D Page Database: A Tool for Proteomics Study of Diabetes and Obesity," Proteomics, vol. 1, No. 1, pp. 136-163 (Jan. 2001).

Jason Sulkowski et al., "SIRP Signaling Modulates Neuronal Akt," Journal of Neurovirology, vol. 9, Supp(3), p. 82 (2003).

Mark A. Watson et al., "Clinical Utility of Biochemical Analysts of Cerebrospinal Fluid," Clinical Chemistry, vol. 41, No. 3, pp. 343-360 (1995).

Brett R. Wenner et al., "Proteomic Analysis of Human Ventricular Cerebrospinal Fluid from Neurologically Normal, Elderly Subjects Using Two-Dimensional LC-MS/MS," Journal of Proteome Research, vol. 3, No. 1, pp. 97-103 (2004).

Xianglin Yuan et al., "Analysis of the Human Lumbar Cerebrospinal Fluid Proteome," Electrophoresis, vol. 23, No. 7-8, pp. 1185-1196 (Apr. 2002).

Xianglin Yuan et al., "Proteomics Analysis of Prefractionated Human Lumbar Cerebrospinal Fluid," Proteomics, vol. 5, No. 2, pp. 541-550 (Feb. 2005).

Jing Zhang et al., "Quantitative Proteomic Analysis of Age-Related Changes in Human Cerebrospinal Fluid," Neurobiology of Aging, vol. 26, No. 2, pp. 207-227 (Feb . 2005).

Sano, T. et al. "Molecuar Biology and Boechnology", ed. Robert A. Meyers, VCH Publishers Inc., 1995, pp. 458-460.

Robers, M. et al , "Development of a Rapid Microparticie-enhanced Turbidimetric Immunoassay for Plasma Fatty Acid-binding Protein, an Early Marker of Acute Myocardial Infarction", Clinical Chemistry, vol. 44, No. 7, 1993, pp. 1564-1567.

Blum, H. et al., "Improved silver staining of plant proteins, RNA and DNA in polyacrylamide gels", Electrophoresis, vol. 8, 1987, pp. 93-99.

Scherl, A et al., "Functional Proteomc Analysis of Human Nuceolus", Moecuar Bioogy of the Cell, vol. 13, Nov. 2002, pp. 4100-4109.

Towbin, H. et al., "Electrophoretic transfer of proteins from polyacrylamide gels to nitrocellulose sheets: Procedure and some applications", Proc. Natl. Acad. Sci. USA, vol. 76, No. 9, Sep. 1979, pp. 4350-4354.

Vaagenes, P. et al., "Enzyme Level Changes in the Cerebrospinal Fluid of Patients With Acute Stroke", Arch Neural, vol. 43, Apr. 1986, pp. 357-362.

Hochstrasser, D. et al. "'Catalyst,' for polyacrylamide gel polymerization and detection of proteins by silver staining", Applied and Theoretical Electrophoresis, vol. 1, 1988, pp. 35-40.

\* cited by examiner

Figure 5. UFD1 detection in new plasma samples 2 fold diluted. Antibodies sandwich immunofluorescent ELISA. Crude values kinetic mode. Controls/stroke matched age/sex Figure 6. ROC curve of UFD1

UFD1 best cutoff value to differentiate stroke vs control. Determination of sensitivity and specificity Figure 7 - UFDP1 plasma concentration: ELISA

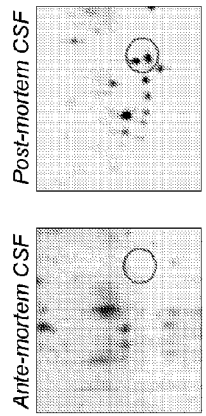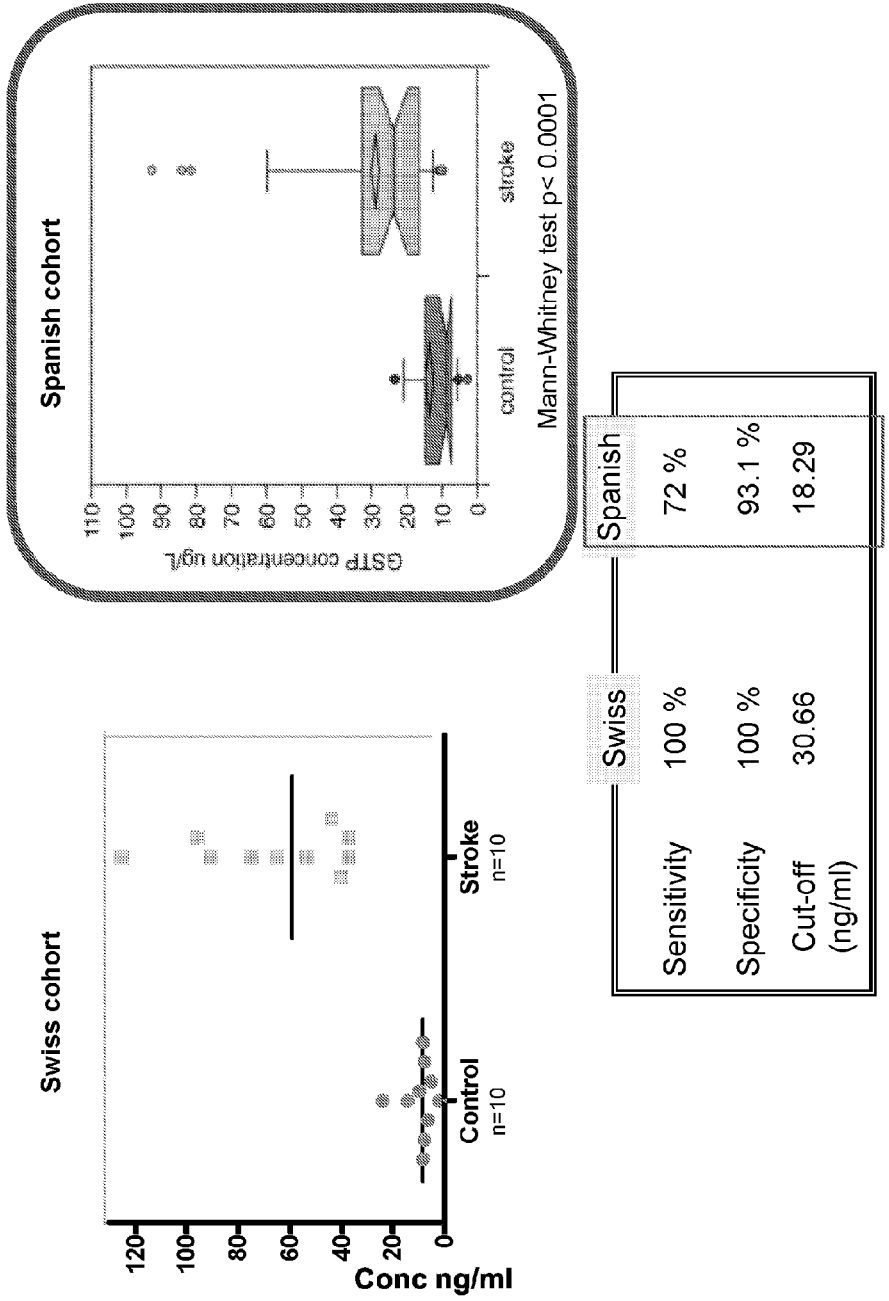
FIGURE 9
GSTP1-1
(Glutathion-S-Transferase Protein 1-1)

Western blot validation of Apoliproprotein A-IV in
Alzheimer's disease.

Key:
C - Control patient plasma; A - Alzheimer's patient plasma

Scatter plot with the measured values of 20 case and 20 control human plasma samples from experiment VL050802.

Correlation of complement factor H levels determined by western blot with Global Dementia Scale in patients with presumed Alzheimer's disease. Error bars represent standard deviation. CFH levels in arbitrary units.

Receiver Operating Curve (ROC) for complement factor H and alpha-2-macroglobulin as candidate plasma biomarkers of Alzheimer's disease

DIAGNOSTIC METHOD FOR BRAIN DAMAGE-RELATED DISORDERS

This application is a National Stage entry of International Application No. PCT/GB2006/050207, filed Jul. 14, 2006, the entire specification, claims, and drawings of which are incorporated herewith by reference.

BACKGROUND OF THE INVENTION

1. Field of the Invention

This invention relates to a diagnostic method for brain damage-related disorders.

No biological marker is currently available for the routine diagnosis of brain damage-related disorders including cerebrovascular, dementia and neurodegenerative diseases. This invention relates to the use of cerebrospinal fluid from deceased patients as a model for the discovery of brain damage-related disorder markers, and to the use of such markers in diagnosis of human and animal brain damage-related disorders.

2. Description of the Related Art

Over the last two decades, a number of biological markers (biomarkers) have been studied in the cerebrospinal fluid (CSF) and serum of patients with brain damage-related disorders, including creatine kinase-BB [1], lactate dehydrogenase [2], myelin basic protein [3], S100 protein [4], neuron-specific enolase (NSE) [5], glial fibrillary acidic protein [6] and tau [7]. Most of them have not proved useful indicators of the extent of brain damage and accurate predictors of clinical status and functional outcome. In fact, the diagnostic value of biomarkers for brain damage-related disorders has been hampered by their late appearance and a delayed peak after the damage event, their poor sensitivity and specificity, and the limited understanding of the mechanisms governing the release of these molecules into the CSF and ultimately in the blood. As a result of these limitations, the use of brain damage-related disorder biomarkers is currently limited to research settings and none has been recommended for routine assessment [8].

WO 01/42793 relates to a diagnostic assay for stroke in which the concentration of heart or brain fatty acid binding protein (H-FABP or B-FABP) is determined in a sample of body fluid.

SUMMARY OF THE INVENTION

Ideally, a biomarker for the diagnosis, monitoring and prognosis of brain damage-related disorders should include at least the following characteristics: (1) it should be brain-specific; (2) because of obvious difficulties to obtain CSF samples in patients, detection in more readily available body fluids such as blood, serum, plasma, urine, saliva or tears is highly desirable; (3) it should appear very early; (4) its peak level, alternatively the area under the curve of sequential concentrations, should reflect the extent of brain damage; finally (5) it should be indicative of functional outcome. We demonstrate here new brain damage-related disorder biomarkers.

We describe how proteins have been identified as new diagnostic biomarkers for brain damage-related disorders using a proteomics-based analysis of CSF from deceased patients as a model of massive brain damage. Diagnostic assays for stroke based on such markers using FABP's have been described in WO 01/42793 and using RNA-BP, UFD1 and NDKA have been described in WO2005/029088. Diagnostic assays for Huntington's disease using clusterin have been described in WO 2006/061610. Diagnostic assays for Alzheimer's disease using Apolipoprotein A-IV, complement factor H, complement factor 3a and alpha-2-macroglobulin have been described in WO 2006/035237. Diagnostic assays for Creutzfeld-Jakob disease (CJD) and its variant form vCJD using FABP's have been described in WO 01/67108, and similar assays based on haemoglobin isoforms and cystatin C have been described in WO 2004/040316. A further diagnostic assay for CJD and vCJD based on haemoglobin beta has been described in WO 2006/061609. Methods and compositions relating to Alzheimer's disease are disclosed in WO 2006/021810. Use of the polypeptides according to the present invention can be validated in a similar way.

According to a first object of the invention, compositions are provided which comprise polypeptides for which the level was found either increased or decreased in the cerebrospinal fluid from deceased patients compared to cerebrospinal fluid from healthy donors. According to this same object, compositions are disclosed which comprise antibodies which are derived from the above polypeptides According to a second object of the invention, methods are provided which utilize the inventive compositions in the diagnosis and prognosis of brain damage-related disorders including cerebrovascular, dementia and neurodegenerative diseases. Such methods may be carried out in vitro.

The present invention provides the following:

1. A method of diagnosis of a brain damage-related disorder or the possibility thereof in a subject suspected of suffering therefrom, which comprises detecting at least one polypeptide, or a variant, mutant or isoform thereof, in a sample of body fluid taken from the subject, wherein the polypeptide is one for which the level is either increased or decreased in cerebrospinal fluid from deceased patients compared to cerebrospinal fluid from healthy donors.

2. A method of diagnosis of a brain damage-related disorder or the possibility thereof in a subject suspected of suffering therefrom, which comprises detecting at least one polypeptide, or a variant, mutant or isoform thereof, selected from Table 1 below in a sample of body fluid taken from the subject.

3. A method of diagnosis of a brain damage-related disorder or the possibility thereof in a subject suspected of suffering therefrom, which comprises detecting at least one polypeptide, or a variant, mutant or isoform thereof, selected from Table 2 herein in a sample of body fluid taken from the subject.

4. A method of diagnosis of a brain damage-related disorder or the possibility thereof in a subject suspected of suffering therefrom, which comprises detecting at least one polypeptide, or a variant, mutant or isoform thereof, selected from Table 3 herein in a sample of body fluid taken from the subject.

5. A method of diagnosis of a brain damage-related disorder or the possibility thereof in a subject suspected of suffering therefrom, which comprises detecting at least one polypeptide, or a variant, mutant or isoform thereof, selected from Table 4 herein in a sample of body fluid taken from the subject.

6. A method of following the progression of a brain damage-related disorder in a subject previously diagnosed as suffering therefrom, which comprises measuring the levels of at least one polypeptide, or a variant, mutant or isoform thereof, selected from Table 1, 2, 3 or 4 herein in multiple samples of body fluid taken from the subject at different times and determining the change in levels of the at least one polypeptide in the most recently tested sample compared to levels in previously tested samples and correlating such change to the progression, regression or stabilization of said brain damage-related disorder.

7. A method according to any of 1 to 6, in which the at least one polypeptide is differentially contained in the body fluid of brain damage-related disorder-affected subjects and non-brain damage-related disorder-affected subjects (control subjects), and the method includes determining whether the concentration of polypeptide in the sample is consistent with that found in patients with a brain damage-related disorder, thereby providing diagnosis of a brain damage-related disorder.

8. A method according to any of 1 to 7, in which an antibody to the at least one polypeptide is used in the detection or the determination of the concentration.

9. A method according to any of 1 to 8, in which the body fluid is cerebrospinal fluid, plasma, serum, blood, tears, urine or saliva.

10. A method according to any of 1 to 9, in which the at least one polypeptide is present in the body fluid of brain damage-related disorder-affected subjects and not present in the body fluid of non-brain damage-related disorder-affected subjects, whereby the presence of the at least one polypeptide in a body fluid sample is indicative of a brain damage-related disorder.

11. A method according to any of 1 to 9, in which the at least one polypeptide is not present in the body fluid of brain damage-related disorder-affected subjects and present in the body fluid of non-brain damage-related disorder-affected subjects, whereby the non-presence of the at least one polypeptide in a body fluid sample is indicative of brain damage-related disorder.

12. A method according to any of 1 to 11, in which the presence, absence and/or amount of a plurality of peptides is determined in the sample.

13. A method according to any of 1 to 12, in which one or more specific isoforms of the at least one polypeptide are determined.

14. A method according to 13, in which diagnosis is made on the basis of differing levels of specific isoforms of the at least one polypeptide.

15. A method according to any of 1 to 14, in which the at least one polypeptide is differentially subject to post-translational modification in the body fluid of brain damage-related disorder-affected subjects and non-brain damage-related disorder-affected subjects, and the method includes detecting the post-translational modification of the polypeptide in the sample and determining whether this is consistent with that found in patients with a brain damage-related disorder, thereby providing diagnosis of a brain damage-related disorder.

16. A method according to 15, in which the post-translational modification comprises N-glycosylation.

17. A method according to any of 1 to 16, in which the at least one polypeptide is detected by determination of at least one autoantibody thereto.

18. A method according to any of 1 to 17, in which two or more markers selected from antibodies to the at least one polypeptide are used in a single well of an ELISA microtiter plate.

19. A method according to any of 1 to 18, in which two or more of the polypeptides are separately assayed, and a predictive algorithm is used for diagnosis.

20. Use of a polypeptide, or a variant or mutant thereof, wherein the polypeptide is one for which the level is either increased or decreased in cerebrospinal fluid from deceased patients compared to cerebrospinal fluid from healthy donors, or wherein the polypeptide is selected from Table 1, 2, 3 or 4, or a combination of such polypeptides, for diagnostic, prognostic and therapeutic applications relating to brain damage-related disorders, or in the manufacture of a medicament for treatment of a brain damage-related disorder.

21. Use according to 20, in which the or each polypeptide is differentially contained in a body fluid of brain damage-related disorder-affected subjects and subjects not affected by a brain damage-related disorder.

22. Use according to 20 or 21, in which a vaccine directed against a polypeptide, or a variant or mutant thereof, or an antigenic determinant thereof, is administered to a subject, wherein the polypeptide is one for which the level is either increased or decreased in cerebrospinal fluid from deceased patients compared to cerebrospinal fluid from healthy donors, or wherein the polypeptide is selected from Table 1, 2, 3 or 4.

23. Use for diagnostic, prognostic and therapeutic applications, relating to brain damage-related disorders, or in the manufacture of a medicament for treatment of a brain damage-related disorder, of a material which recognises, binds to or has affinity for a polypeptide, or a variant or mutant thereof, wherein the polypeptide is one for which the level is either increased or decreased in cerebrospinal fluid from deceased patients compared to cerebrospinal fluid from healthy donors, or wherein the polypeptide is selected from Table 1, 2, 3 or 4.

24. Use according to 23 of a combination of materials, each of which respectively recognises, binds to or has affinity for a polypeptide, or a variant or mutant thereof, wherein the polypeptide is one for which the level is either increased or decreased in cerebrospinal fluid from deceased patients compared to cerebrospinal fluid from healthy donors, or wherein the polypeptide is selected from Table 1, 2, 3 or 4.

25. Use according to 23 or 24, in which the or each material is an antibody or antibody chip.

26. Use according to 25, in which the material is an antibody with specificity for any polypeptide for which the level is either increased or decreased in cerebrospinal fluid from deceased patients compared to cerebrospinal fluid from healthy donors, or listed in Table 1, 2, 3 or 4, or a variant or mutant thereof.

27. An assay device for use in the diagnosis of brain damage-related disorders, which comprises a solid substrate having a location containing a material, which recognizes, binds to or has affinity for a polypeptide, or a variant or mutant thereof, or an autoantibody thereof, wherein the polypeptide is one for which the level is either increased or decreased in cerebrospinal fluid from deceased patients compared to cerebrospinal fluid from healthy donors, or wherein the polypeptide is selected from Table 1, 2, 3 or 4.

28. An assay device according to 27, in which the solid substrate has a plurality of locations each respectively containing a material which recognizes, binds to or has affinity for a polypeptide, or a variant or mutant thereof, or an autoantibody thereof, wherein the polypeptide is one for which the level is either increased or decreased in cerebrospinal fluid from deceased patients compared to cerebrospinal fluid from healthy donors, or wherein the polypeptide is selected from Table 1, 2, 3 or 4.

29. An assay device according to 27 or 28, in which the material is an antibody or antibody chip.

30. An assay device according to 29, which has a unique addressable location for each of a plurality of antibodies to said polypeptides, thereby to permit an assay readout for each individual polypeptide or for any combination of polypeptides.

31. An assay device according to 27 or 28, which has a unique addressable location for each of a plurality of said polypeptides, thereby to permit an assay readout for each individual autoantibody of a polypeptide or for any combination of autoantibodies of said polypeptides.

32. An assay device according to any of 27 to 31, including an antibody to any polypeptide for which the level is either increased or decreased in cerebrospinal fluid from deceased patients compared to cerebrospinal fluid from healthy donors, or listed in Table 1, 2, 3 or 4, or a variant or mutant thereof.

33. An assay device according to any of 27 to 32, further having a location containing a material which recognizes, binds to or has affinity for glutathione S transferase P.

34. An assay device according to 33, in which the material is an antibody or antibody chip.

35. A kit for use in the diagnosis of brain damage-related disorders, comprising an assay device according to any of 27 to 34, and means for detecting the amount of one or more of the polypeptides in a sample of body fluid taken from a subject.

The polypeptides (also referred to as proteins) useful in the present invention are those for which the level was found either increased or decreased in the cerebrospinal fluid from deceased patients compared to cerebrospinal fluid from healthy donors. In this context, the term "increased" means that the polypeptide occurs exclusively in deceased CSF as opposed to healthy CSF, or that it occurs in deceased CSF at a higher level than in healthy CSF, such as at least 1.2 fold higher, preferably at least 1.5 fold higher, or even at least 8-10 fold higher. The term "decreased" means that the polypeptide is absent in deceased CSF as opposed to healthy CSF, or that it occurs in deceased CSF at a lower level than in healthy CSF, such as lower by a factor of 0.8 or less, preferably 0.7 or less.

It is a reasonable prediction that all such polypeptides will be useful as markers for brain damage-related disorders. This has been validated for certain polypeptides, as described in the Examples below. The use of other polypeptides has been validated by data in WO 01/42793; WO 01/67108; WO2004/040316; WO 2005/029088; WO 2006/035237; WO 2006/061609; and WO 2006/061610; all of which are incorporated herein by reference.

The polypeptides (also referred to as proteins) useful in the present invention are not restricted to the sequences corresponding to the accession numbers in Tables 1, 2, 3 and 4, and include variants, mutants and isoforms thereof. A variant is defined as a naturally occurring variation in the sequence of a polypeptide which has a high degree of homology with the given sequence, and which has substantially the same functional and immunological properties. A mutant is defined as an artificially created variant. A high degree of homology is defined as at least 90%, preferably at least 95% and most preferably at least 99% homology. Variants may occur within a single species or between different species. An isoform of a polypeptide has the same function as the polypeptide but is encoded by a different gene and may have small differences in its sequence. The above proteins are of human origin, but the invention encompasses use of the corresponding polypeptides from other mammalian species, e.g. bovine animals.

Brain damage-related disorders in the context of the present invention include the following: head trauma, ischemic stroke, hemorrhagic stroke, subarachnoid hemorrhage, intra cranial hemorrhage, transient ischemic attack, vascular dementia, corticobasal ganglionic degeneration, encephalitis, epilepsy, Landau-Kleffner syndrome, hydrocephalus, pseudotumor cerebri, thalamic diseases, meningitis, myelitis, movement disorders, essential tremor, spinal cord diseases, syringomyelia, Alzheimer's disease (early onset), Alzheimer's disease (late onset), multi-infarct dementia, Pick's disease, Huntingdon's disease, Parkinson, Parkinson syndromes, frontotemporal dementia, corticobasal degeneration, multiple system atrophy, progressive supranuclear palsy, Lewy body disease, amyotrophic lateral sclerosis, Creutzfeldt-Jakob disease, Dandy-Walker syndrome, Friedreich ataxia, Machado-Joseph disease, migraine, schizophrenia, mood disorders and depression. Corresponding disorders in non-human mammals are also included, such as transmissible spongiform encephalopathies (TSEs), e.g. bovine spongiform encephalopathy (BSE) in cattle or scrapie in sheep. The term "patient" accordingly encompasses both humans and non-human mammals.

In one embodiment the brain damage-related disorder is stroke and the polypeptide is a homolog of one of the proteins listed in Table 1, 2, 3 or 4.

The term "diagnosis", as used herein, includes determining whether a brain damage-related disorder is present or absent, and may also include determining the stage to which it has progressed. The diagnosis can serve as the basis of a prognosis as to the future outcome for the patient and for monitoring efficacy of treatment.

The term "control" refers to a normal subject (human or non-human mammal), i.e. one not suffering from a brain damage-related disorder (also called a "healthy donor"), and also to a sample taken from the same subject that provided the diagnostic sample, but at an earlier time.

References to an increased or decreased concentration compared with a sample of a control do not imply that a step of comparing is actually undertaken, since in many cases it will be obvious to the skilled practitioner that the concentration is abnormally high or low. Further, when the stages of a brain damage-related disorder are being monitored progressively, the comparison made can be with the concentration previously seen in the same subject in earlier progression of the disorder.

BRIEF DESCRIPTION OF THE DRAWINGS

FIG. 9 shows results of an assay for GSTP-1 for groups of stroke patients and controls, as described in Example 5.

DESCRIPTION OF PREFERRED EMBODIMENTS

Figure 1:
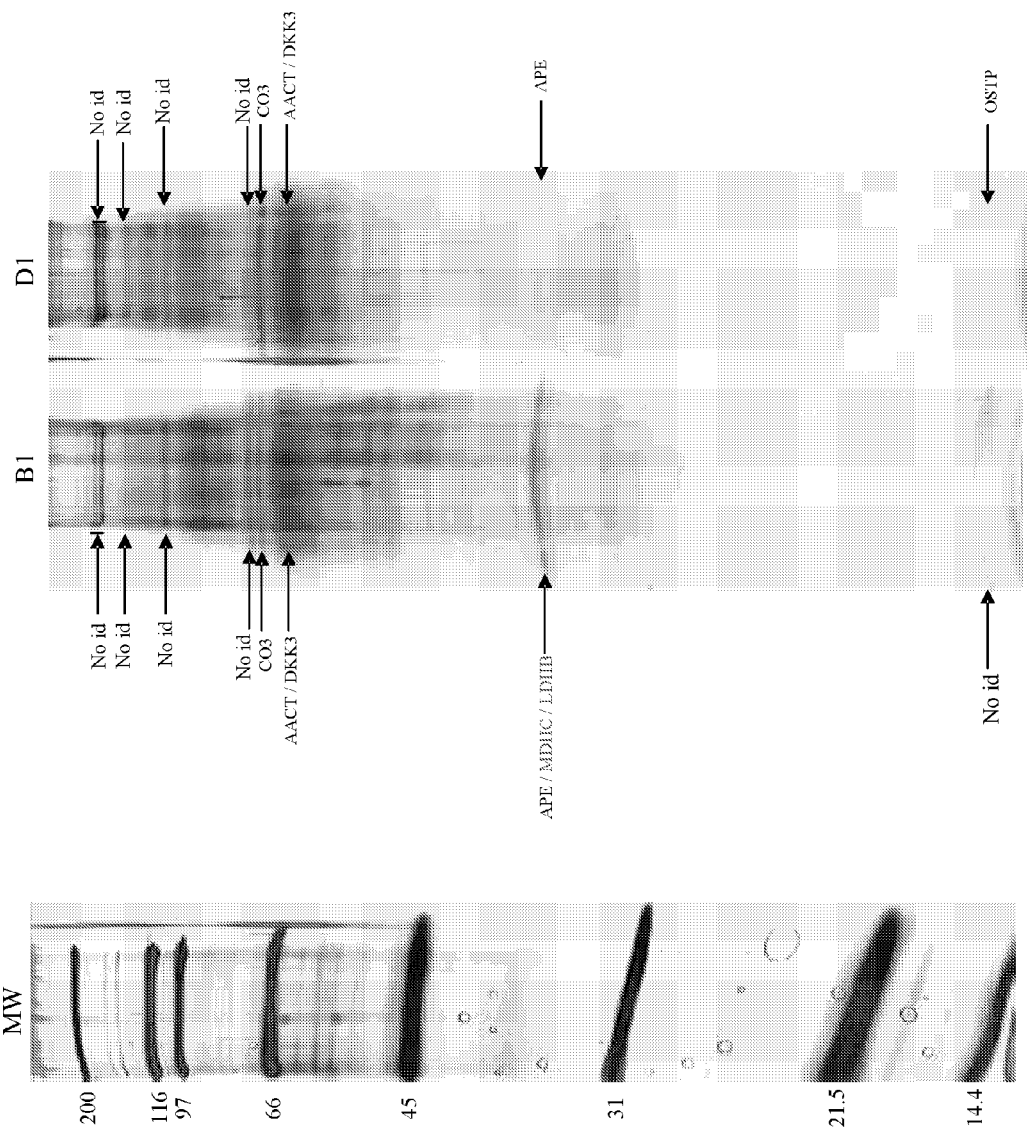
FIGS. 1-4 show portions of 1-DE maps after Off-gel electrophoresis for ante- and post-mortem CSF, with arrows indicating bands corresponding to proteins listed in Table 1. 5-10 μg of protein was loaded on a SDS PAGE slab gel (12.5% T/2.6% C). The gel was silver stained.

The invention presented here is directed towards compositions and methods for detecting increasing or reducing polypeptides levels in body fluids including blood components (e.g. plasma or serum) or cerebrospinal fluid from subjects affected by a brain damage-related disorder including cerebrovascular, dementia and neurodegenerative diseases, as compared with control (non-affected) subjects. For this purpose, use can be made of antibodies or any specific polypeptide detection method.

The invention also includes embodiments where the polypeptides, in particular those of Table 1, 2, 3 or 4, are determined indirectly. For example, at least one autoantibody to one or more of the polypeptides, in particular those of Table 1, 2, 3 or 4, may be determined.

Antibodies against brain damage protein markers, in particular their protein-binding domains, are suitable as detection tools. Molecular biological and biotechnological methods can be used to alter and optimize the antibody properties of the said molecules in a specific manner. In addition to this, the antibodies can be modified chemically, for example by means of acetylation, carbamoylation, formylation, biotinylation, acylation, or derivatization with polyethylene glycol or hydrophilic polymers, in order to increase their stability.

A specific polypeptide marker selected from any of the proteins listed in Table 1, 2, 3 or 4 is determined in a body fluid sample, for example by using an antibody thereto. The marker may simply be detected and/or its concentration may be measured. The marker is preferably measured by an immunoassay, using a specific antibody to the polypeptide and measuring the extent of the antigen (polypeptide)/antibody interaction. The antibody may be a monoclonal antibody or an engineered (chimeric) antibody. Antibodies to the polypeptides are known and are commercially available. Also, the usual Köhler-Milstein method may be used to raise antibodies. Less preferably, the antibody may be polyclonal. In the context of the present invention, the term "antibodies" includes binding fragments of antibodies, such as single chain or Fab fragments.

Any known method of immunoassay may be used. In a sandwich assay an antibody (e.g. polyclonal) to the polypeptide is bound to the solid phase such as a well of a plastics microtitre plate, and incubated with the sample and with a labelled second antibody specific to the polypeptide to be detected. Alternatively, an antibody capture assay (also called "indirect immunoassay") can be used. Here, the test sample is allowed to bind to a solid phase, and the anti-polypeptide antibody (polyclonal or monoclonal) is then added and allowed to bind. If a polyclonal antibody is used in this context, it should desirably be one which exhibits a low cross-reactivity with other forms of polypeptide. After washing away unbound material, the amount of antibody bound to the solid phase is determined using a labeled second antibody, anti- to the first.

A direct assay can be performed by using a labelled anti-polypeptide antibody. The test sample is allowed to bind to the solid phase and the anti-polypeptide antibody is added. After washing away unbound material, the amount of antibody bound to the solid phase is determined. The antibody can be labeled directly rather than via a second antibody.

In another embodiment, a competition assay can be performed between the sample and a labeled polypeptide or a peptide derived therefrom, these two antigens being in competition for a limited amount of anti-polypeptide antibody bound to a solid support. The labeled polypeptide or peptide can be pre-incubated with the antibody on the solid phase, whereby the polypeptide in the sample displaces part of the polypeptide or peptide thereof bound to the antibody.

In yet another embodiment, the two antigens are allowed to compete in a single co-incubation with the antibody. After removal of unbound antigen from the support by washing, the amount of label attached to the support is determined and the amount of protein in the sample is measured by reference to standard titration curves established previously.

Throughout, the label is preferably an enzyme. The substrate for the enzyme may be color-forming, fluorescent, chemiluminescent or electrochemical, and can be soluble or precipitating. Alternatively, the label may be a radioisotope or fluorescent, e.g. using conjugated fluorescein.

The enzyme may, for example, be alkaline phosphatase or horseradish peroxidase and can conveniently be used calorimetrically, e.g. using p-nitrophenyl phosphate as a yellow-forming substrate with alkaline phosphatase.

For a chemiluminescent assay, the antibody can be labeled with an acridinium ester or horseradish peroxidase. The latter is used in enhanced chemiluminescent (ECL) assay. Here, the antibody, labeled with horseradish peroxidase, participates in a chemiluminescent reaction with luminol, a peroxide substrate and a compound, which enhances the intensity and duration of the emitted light, typically, 4-iodophenol or 4-hydroxycinnamic acid.

An amplified immunoassay such as immuno-PCR can be used. In this technique, the antibody is covalently linked to a molecule of arbitrary DNA comprising PCR primers, whereby the DNA with the antibody attached to it is amplified by the polymerase chain reaction. See E. R. Hendrickson et al., Nucleic Acids Research 1995; 23, 522-529 (1995) or T. Sano et al., in "Molecular Biology and Biotechnology" ed. Robert A. Meyers, VCH Publishers, Inc. (1995), pages 458-460. The signal is read out as before.

In one procedure, an enzyme-linked immunosorbent assay (ELISA) can be used to detect the polypeptide.

The full automation in a widely used clinical chemistry analyser such as the COBAS™ MIRA Plus system from Hoffmann-La Roche, described by M. Robers et al. Clin Chem. 1998 July; 44(7):1564-7 or the AxSYM™ system from Abbott Laboratories, is possible and can be applied for routine clinical diagnosis of brain damage-related disorders.

The polypeptide concentrations can be measured by other means than immunoassay. For example, the sample can be subjected to 2D-gel electrophoresis and the amount of the polypeptide estimated by densitometric scanning of the gel or of a blot therefrom. However, it is desirable to carry out the assay in a rapid manner, so that the patient can be treated promptly.

In principle, any body fluid can be used to provide a sample for diagnosis, but preferably the body fluid is cerebrospinal fluid (CSF), plasma, serum, blood, urine, tears or saliva.

According to the invention, a diagnosis of brain damage-related disorders may be made from determination of a single polypeptide or any combination of two or more of the polypeptides.

The invention also relates to the use of one or more of the specified polypeptides which is differentially contained in a body fluid of brain damage-affected subjects and non-brain damage-affected subjects, for diagnostic, prognostic and therapeutic applications, including for the manufacture of a medicament for treatment of a brain damage-related disorder. This may involve the preparation and/or use of a material which recognizes, binds to or has some affinity to the above-mentioned polypeptide. Examples of such materials are antibodies and antibody chips. The term "antibody" as used herein includes polyclonal antiserum, monoclonal antibodies, fragments of antibodies such as Fab, and genetically engineered antibodies. The antibodies may be chimeric or of a single species. The above reference to "prognostic" applications includes making a determination of the likely course of a brain damage-related disorder by, for example, measuring the amount of the above-mentioned polypeptide in a sample of body fluid. The above reference to "therapeutic follow-up" applications includes making a determination of the likely course of a brain damage-related disorder by, for example, measuring the amount of the above-mentioned polypeptide in a sample of body fluid (and evaluating its level as a function of the treatment, the disability recovery or not, the size of the lesions etc.). The above reference to "therapeutic" applications includes, for example, preparing materials which recognize, bind to or have affinity to the above-mentioned polypeptides, and using such materials in therapy. The materials may in this case be modified, for example by combining an antibody with a drug, thereby to target the drug to a specific region of the patient. In a further embodiment, a vaccine directed against a polypeptide, or a variant or mutant thereof, selected from Table 1, 2, 3 or 4, or an antigenic determinant (epitope) thereof, is administered to a subject.

The above reference to "presence" or "absence" of a polypeptide, and the equivalent expressions "present" and "not present", should be understood to mean simply that there is a significant difference in the amount of a polypeptide which is detected in the affected and non-affected (or control) sample. Thus, the "absence" of a polypeptide in a test sample may include the possibility that the polypeptide is actually present, but in a significantly lower amount than in a comparative test sample. According to the invention, a diagnosis can be made on the basis of the presence or absence of a polypeptide, and this includes the presence of a polypeptide in a significantly lower or significantly higher amount with reference to a comparative (or control) test sample.

The above references to "detecting" a polypeptide should be understood to include a reference to compositions and methods for detecting post-translational modifications of the polypeptides in addition to quantitative variations. The invention therefore encompasses the detection of post-translational modifications in general, and determining whether such modifications of a polypeptide are consistent with a diagnosis of a brain damage-related disorder. One example of such post-translational modification is N-glycosylation.

Kits and assay devices for use in diagnosis of brain damage-related disorders are also within the scope of the invention. These may include one or more antibodies to a polypeptide selected from any of the proteins listed in Table 1, 2, 3 or 4. The antibodies will bind to the appropriate polypeptides in a fluid sample taken from a patient. The antibodies may be immobilised on a solid support. Preferably, each antibody is placed in a unique addressable location, thereby to permit separated assay readout for each individual polypeptide in the sample, as well as readouts for any selected combination of polypeptides. Such kits and assay devices may also include antibodies to other marker polypeptides in addition to one or more of those in Table 1, 2, 3 or 4. Such other marker polypeptides include those described in WO01/42793 and WO2005/029088. In one particular embodiment, the other marker polypeptide is glutathione S transferase P.

An assay device according to the invention may comprise a solid substrate having one or more locations containing a material which recognizes, binds to or has affinity for a polypeptide, or a variant or mutant thereof, as defined above, in particular selected from Table 1, 2, 3 or 4. Preferred polypeptides which may be detected by such a device are fatty acid binding proteins, glutathione S transferase P, RNA-BP, UFD1, NDKA, clusterin, Apolipoprotein A-IV, complement factor H, complement factor 3a, alpha-2-macroglobulin, haemogobin isoforms, cystatin C, haemoglobin beta, Apolipoprotein E, Glutathione S-transferase Mu 1, Tubulin beta-4 chain, Ubiquitin carboxyl-terminal hydrolase isozyme L1, Transgelin 3, Neuronal protein Np25, Rab GDP dissociation inhibitor 1, Dihydropyrimidinase-like 2 (DRP-2), Aspartate aminotransferase cytoplasmic, Fructose-bisphosphate aldolase C, and Proteasome subunit alpha type 6. The assay device may include antibodies to two or more of these polypeptides, to three or more, four or more, five or more, or in some cases ten or twenty or more.

The following Examples illustrate the invention.

ABBREVIATIONS

CSF: cerebrospinal fluid; H-FABP: heart fatty acid-binding protein; NDKA: nucleoside diphosphate kinase A; CJD: Creutzfeldt-Jakob disease; OGE: off-gel electrophoresis; UFD1: ubiquitin fusion degradation protein 1; GST-P: glutathione S-transferase P; SBPs: spectrin breakdown products.

Example 1

Using one-dimensional gel electrophoresis (1-DE) separation of cerebrospinal fluid (CSF) proteins and mass spectrometry techniques, 58 polypeptides named in Table 1 were found elevated or decreased in the CSF of deceased patients, used as a model of massive brain damage.

Study Population and Sample Handling

Twenty CSF samples were used for the proteomics-based approach aiming at discovering brain damage-related disorder markers. Five of these samples were obtained at autopsy from deceased patients 6 hours after death with no pathology of the central nervous system. Fifteen others were collected by lumbar puncture from living patients who had a neurological workup for benign conditions unrelated to brain damage (atypical headache and idiopathic peripheral facial nerve palsy). CSF samples were centrifuged immediately after collection, aliquoted, frozen at −80° C. and stored until analysis.

CSF Depletion Fractionation

Immunodepletion of human serum albumin, transferrin, haptoglobin, IgG, IgA and antitrypsin was performed using a Multiple Affinity Removal System (Agilent Technologies, Wilmington, USA). 3 ml of CSF was concentrated to approximately 300 µl using ultrafiltration (10 kDa MWCO, Vivascience). The CSF was divided into 200 µl aliquots for immunodepletion according to the manufacturer's instructions. Combined fractions following depletion were concentrated using ultrafiltration. Final CSF protein concentrations of between 600 and 900 µg/µl were measured using a Bradford assay. All reagents and apparatus for off-gel electrophoresis (OGE) have been described in detail elsewhere (Ros, A., et al., *Protein purification by Off-Gel electrophoresis*. Proteomics, 2002. 2(2): p. 151-6). 750 µl of the immunodepleted CSF samples were loaded on the strip for OGE using all-well loading (50 µl per well). The samples were focused for a total of 31.6 kVhrs (1 hr at 100 V, 1 hr at 500 V, 1 hr at 1000 V, 15 hrs at 2000 V). The current was limited to 50 µA and the temperature was controlled at 20° C. Fractions (20-100 µl) were collected from each well and stored at −20° C. prior to SDS-PAGE.

1-DE of OGE Fractionated CSF Proteins

Fractions from OGE were mixed with a 5× concentrated solution of Laemmli's buffer (0.125 M Tris-HCl, 4% SDS, 40% glycerol, 0.1% bromophenol blue, pH 6.8) up to 70 µl and heated at 95° C. for 5 min. Samples were centrifuged at 14000 g and supernatant loaded on the 12.5% SDS-polyacrylamide gel. Migration was performed in a Tris-Glycine-SDS pH 8.3 buffer. The gel was then stained using MS compatible silver staining derived from Blum [Blum, H., Beier, H. and Gross, H. J., *Electrophoresis* 1987, 8, 93-99]. The gel was first fixed for a minimum of 30 min 50% (v/v) methanol 10% (v/v)

acetic acid and then 15 min in 5% (v/v) methanol. The gel was then washed 3 times 5 min in milli-Q H$_2$O and incubated 2 min in 0.2 g/L (w/v) fresh sodium thiosulfate (Na$_2$S$_2$O$_3$, 5H$_2$O). The gel was further washed 3 times 30 sec in milli-Q H$_2$O, and incubated in the staining solution, i.e. 25 min in 2 g/L silver nitrate (AgNO$_3$) solution. The gel was washed 3 times 1 min in milli-Q H$_2$O, and incubated in the developing solution (sodium carbonate Na$_2$CO$_3$ 30 g/L (w/v), 0.05% of 37% HCOH (v/v), 2% (v/v) of a fresh 0.2 g/L (w/v) sodium thiosulfate (Na$_2$S$_2$O$_3$, 5H$_2$O)) for 10 min maximum. The gel development was stopped using a 14 g/l (w/v) Na$_2$-EDTA solution for 10 min before washing in milli-Q H$_2$O. The apparent molecular masses were determined by running 2 µg of broad range molecular weight standards (Bio-Rad, Hercules, Calif., USA). The gel was scanned on a Arcus II Agfa scanner, with Agfa Fotolook version 3.6 software. Bands to be identified were cut, placed in an Eppendorf tubes and destained. Each gel piece was incubated in 30 µl destaining solution (30 mM K$_3$FeCN$_6$, 100 mM Na$_2$S$_2$O$_3$) with occasional vortexing until the gels were completely destained (5-10 min). Gel pieces were then washed twice for 10 min with a minimum of 100 µl milli-Q-H$_2$O for 10 and then stored at 4° C. in 10% ethanol (v/v).

Identification of the Proteins by NanoLC-ESI-MS/MS

Gel pieces were washed with 200 µl of 50 mM ammonium bicarbonate, for 10 min. Gel pieces were then dehydrated with 100 µl of 100% CH$_3$CN and dried in a vacuum centrifuge (HETO, Allerod, Denmark). Trypsin digestion was performed as described previously [Scherl, A., Coute, Y., Deon, C., Calle, A., Kindbeiter, K., et al., *Mol Biol Cell* 2002, 13, 4100-9]. NanoLC-ESI-MS/MS was performed on a LCQ DecaXP ion trap (Thermofinnigan, San Jose, Calif.) coupled to a LC-PAL autosampler (CTC Analytics, Zwingen, Switzerland) and a Rheos 2000 Micro HPLC Pump (Flux Instruments, Basel, Switzerland). For each experiment, 5 µl of sample in 5% CH$_3$CN, 0.1% formic acid was injected on a C18 reverse phase column (75 µm inner diameter) packed in house with 5 µm Zorbax 300 Extend-C18 (Agilent Technologies, Wilmington USA). Peptides were eluted from the column using a CH$_3$CN gradient in the presence of 0.1% formic acid. For peptide elution, the acetonitrile concentration was increased from 8 to 47% in 15 min. A flow splitter was used to decrease the flow rate from 40 µl/min to approximately 0.2 µl/min. A 1.8 kV potential was applied on the nano-electrospray capillary (New Objective, Woburn, Mass.). Helium was used as collision gas. The collision energy was set at 35% to the maximum. MS/MS spectra were acquired by automatic switching between MS and MS/MS mode. The two highest peaks from each MS scan were chosen for MS/MS. Dynamic exclusion was applied with a repeat count of 2 and a repeat duration of 0.5 mins. Following these two MSMS acquisitions on the same precursor, the precursor was excluded from MSMS analysis for 1.0 min. Spectra were converted to DTA files, regrouped using in house software and the database search was performed with MASCOT 1.8 (http://www.matrixscience.co.uk/). A tolerance of 2.0 Da was chosen for the precursor and 1.0 Da for fragments. ESI-TRAP was selected as the instrument. The UniProt Swiss-Prot database was searched without species restriction. In these conditions, the threshold of significance was given by a score of 42 or higher by Mascot. The data was also searched against the UniProt SwissProt database using the Phenyx program (http://www.phenyx-ms.com/). Protein hits with less than three peptides above the threshold were manually validated. The data was further searched against the Trembl database, resulting in the identification of a further 22 proteins. The results are shown in Table 1.

TABLE 1

| Post-mortem CSF Accession number | Protein name |
| --- | --- |
| O00241 | Signal-regulatory protein beta-1 |
| O43396 | Thioredoxin-like protein 1 |
| O43488 | Aflatoxin B1 aldehyde reductase member 2 |
| O43707 | Alpha-actinin 4 |
| O75223 | Protein C7orf24 |
| O95336 | 6-phosphogluconolactonase |
| O95861 | 3'(2'),5'-bisphosphate nucleotidase 1 |
| P00352 | Retinal dehydrogenase 1 |
| P00390 | Glutathione reductase, mitochondrial |
| P00491 | Purine nucleoside phosphorylase |
| P00915 | Carbonic anhydrase I |
| P01859 | Ig gamma-2 chain C region* |
| P01876, P01877 | Ig alpha-1 or -2 chain C region |
| P02024 | Hemoglobin beta chain |
| P02545 | Lamin A/C (70 kDa lamin) |
| P02741 | C-reactive protein |
| P02760 | AMBP protein |
| P04642 | L-Lactate dehydrogenase A chain |
| P04746, P04745, P19961 | Alpha-amylase (pancreatic, salivary or 2B) |
| P05089 | Arginase 1 |
| P05209, Q9BQE3 | Tubulin alpha-1 or alpha-6 chain |
| P05413 | Fatty acid-binding protein, heart (H-FABP) |
| P05976 or P06741 | myosin light chain 1 or 3, skeletal muscle isoform |
| P06576 | ATP synthase beta chain, mitochondrial |
| P06753 | Tropomyosin alpha 3 chain |
| P07148 | Fatty acid-binding protein, liver (L-FABP) |
| P07203 | Glutathione peroxidase 1 |
| P07225 | Vitamin K-dependent protein S |
| P07226 | Tropomyosin alpha 4 chain |
| P07237 | Protein disulphide-isomerase |
| P07357 | Complement C8 alpha chain |
| P07738 | Bisphosphoglycerate mutase |
| P07900 | Heat shock protein HSP 90-alpha (HSP 86) |
| P07996 | Thrombospondin 1 |
| P08059 | Glucose-6-phosphate isomerase |
| P08133 | Annexin A6 |
| P08758 | Annexin A5 |
| P09417 | Dihydropteridine reductase |
| P09488 | Glutathione S-transferase Mu 1 |
| P09493 or P06753 | Tropomyosin 1 alpha chain or alpha 3 chain |
| P09525 | Annexin A4 |
| P09668 | Cathepsin H |
| P10586 | Receptor-type tyrosine-protein phosphatase F |
| P10599 | Thioredoxin |
| P10768 | Esterase D |
| P11021 | 78 kDa glucose-regulated protein |
| P12833 | Myosin heavy chain, cardiac muscle beta isoform |
| P12882 | Myosin heavy chain, skeletal muscle, adult 1 |
| P13489 | Placental ribonuclease inhibitor |
| P13535 | Myosin heavy chain, skeletal muscle, perinatal |
| P13611 | Versican core protein |
| P13693 | Translationally controlled tumor protein (TCTP) |
| P13716 | Delta-aminolevulinic acid dehydratase |
| P13929 | Beta enolase |
| P14136 | Glial fibrillary acidic protein, astrocyte (GFAP) |
| P14550 | Alcohol dehydrogenase [NADP+] |
| P14923 | Junction plakoglobin |
| P15103 | Glutamine synthetase |
| P15121 | Aldose reductase |
| P15259 | Phosphoglycerate mutase 2 |
| P15289 | Arylsulfatase A |
| P15924 | Desmoplakin |
| P16930 | Fumarylacetoacetase |
| P17066 | Heat shock 70 kDa protein 6 |
| P18206 | Vinculin |
| P21266 | Glutathione S-transferase Mu 3 |
| P21333 | Filamin A |
| P21695 | Glycerol-3-phosphate dehydrogenase [NAD+], cytoplasmic |
| P22061 | Protein-L-isoaspartate (D-aspartate) O-methyltransferase |

TABLE 1-continued

| | |
|---|---|
| P22314 | Ubiquitin-activating enzyme E1 |
| P23141 | Liver carboxylesterase 1 |
| P24534 | Elongation factor 1-beta |
| P25788 | Proteasome subunit alpha type 3 |
| P26038 | Moesin |
| P26641 | Elongation factor 1-gamma |
| P27169 | Serum paraoxonase/arylesterase 1 |
| P27348 | 14-3-3 protein tau |
| P28072 | Proteasome subunit beta type 6 |
| P28161 | Glutathione S-transferase Mu 2 |
| P28827 | Receptor-type protein-tyrosine phosphatase mu |
| P29218 | Inositol-1 [or 4]-monophosphate |
| P29401 | Transketolase |
| P30040 | Endoplasmic reticulum protein ERp29 |
| P30041 | Peroxiredoxin 6 |
| P30101 | Protein disulfide-isomerase A3 |
| P30626 | Sorcin (22 kDa protein) |
| P31946 | 14-3-3 protein beta/alpha |
| P31948 | Stress-induced-phosphoprotein 1 |
| P34932 | Heat shock 70 kDa protein 4 |
| P35080 | Profilin-2 |
| P35237 | Placental thrombin inhibitor |
| P36980 | Complement factor H-related protein 2 |
| P37837 | Transaldolase |
| P40121 | Macrophage capping protein |
| P42126 | 3,2-trans-enoyl-CoA isomerase, mitochondrial |
| P42655 | 14-3-3 protein epsilon |
| P45381 | Aspartoacylase |
| P46940 | Ras GTPase-activating-like protein IQGAP1 |
| P47756 | F-actin capping protein beta subunit |
| P48637 | Glutathione synthetase |
| P49419 | Aldehyde dehydrogenase family 7 member A1 |
| P50135 | Histamine N-methyltransferase |
| P50395 | Rab GDP dissociation inhibitor beta |
| P52565 | Rho GDP-dissociation inhibitor 1 |
| P52566 | Rho GDP-dissociation inhibitor 2 |
| P52907 | F-actin capping protein alpha-1 subunit |
| P54289 | Dihydropyridine-sensitive L-type, calcium channel alpha-2/delta subunits |
| P54652 | Heat shock-related 70 kDa protein 2 |
| P54922 | ADP-ribosylarginine hydrolase |
| P55287 | Cadherin-11 |
| P55854, P61956 | Ubiquitin-like protein SMT 3A or 3B |
| P57087 | Junctional adhesion molecule 2 |
| P60900 | Proteasome subunit alpha type 6 |
| P61088 | Ubiquitin-conjugating enzyme E2 N |
| P62258 | 14-3-3 protein epsilon |
| P62993 | Growth factor receptor-bound protein 2 |
| P63104 | 14-3-3 protein zeta/delta |
| P68133 | Actin, alpha skeletal muscle |
| Q00169 | Phosphatidylinositol transfer protein alpha isoform |
| Q01082 | Spectrin beta chain, brain 1 |
| Q01995 | Transgelin |
| Q04917 | 14-3-3 protein eta |
| Q06033 | Inter-alpha-trypsin inhibitor heavy chain H3 |
| Q12765 | Secernin 1 |
| Q13332 | Receptor-type tyrosine-protein phosphatase S |
| Q13509 | Tubulin beta-4 |
| Q13740 | CD166 antigen |
| Q13813 | Spectrin alpha chain, brain |
| Q13938 | Calcyphosine |
| Q14126 | Desmoglein 2 |
| Q15149 | Plectin 1 |
| Q15181 | Inorganic pyrophosphatase |
| Q16620 | BDNF/NT-3 growth factors receptor |
| Q16881 | Thioredoxin reductase 1, cytoplasmic |
| Q86UP2 | Kinectin |
| Q86YZ3 | Hornerin |
| Q8N0Y7 | Putative phosphoglycerate mutase 3 |
| Q8TAG5 | Immunoglobulin-like domain protein MGC33530 |
| Q8TD26 | Chromodomain-helicase-DNA-binding protein 6 |
| Q92598 | Heat shock protein 105 kDa |
| Q92890 | Ubiquitin fusion degradation protein 1 homolog |
| Q969H8 | Protein C19 or F10 precursor |
| Q96IU4 | CCG1-interacting factor B |
| Q9BX68 | Histidine triad nucleotide-binding protein 2 |
| Q9H477 | Ribokinase |
| Q9NVS9 | Pyridoxine-5'-phosphate oxidase |
| Q9NZT1 | Calmodulin-like protein 5 |
| Q9P0L0 | Vesicle-associated membrane protein-associated protein A |
| Q9P121 | Neurotrimin |
| Q9UBQ7 | Glyoxylate reductase/hydroxypyruvate reductase |
| Q9UKK9 | ADP-sugar pyrophosphatase |
| Q9UKX2 | Myosin heavy chain, skeletal muscle, adult 2 |
| Q9UN36 | NDRG2 protein |
| Q9Y617 | Phosphoserine aminotransferase |
| Q9Y623 | Myosin heavy chain, skeletal muscle, fetal |
| Ante-mortem CSF | |
| P00748 | Coagulation factor XII |
| P01833 | polymeric-immunoglobulin receptor |
| P04083 | Annexin A1 |
| P04121 | Macrophage capping protein |
| P05109 | Calgranulin A (MRP-8) |
| P12109 | Collagen alpha 1(VI) chain |
| P22352 | Plasma glutathione peroxidase |
| P35247 | Pulmonary surfactant-associated protein D |
| P43121 | Cell surface glycoprotein MUC18 |
| P58876 + others | Histone H2B (different forms) |
| P78509 | Reelin |

| Trembl accession no. | Description |
|---|---|
| O95784 | IgG Fc binding protein (Fragment) |
| Q07898, Q07899, Q07900, Q07901, Q86VB7 | M130 antigen; M130 antigen cytoplasmic variant 1; variant 2; M130 antigen extracellular variant; Similar to CD163 antigen |
| Q7Z664 | Hypothetical protein DKFZp779N0926 (Fragment) |
| Q7Z623 | hypothetical protein |
| Q8IZY7 | Hepatocellular carcinoma associated protein TB6 |
| Q8N240 | Hypothetical protein FLJ34957 |
| Q8N466 | Hypothetical protein with 1 extra peptide over SP entry (Contactin Q12860) |
| Q8NCW5 | ApoA-I binding protein precursor |
| Q8NFZ8 or Q9Y4A4 | TSLC1-like 2 or F22162_1 (Fragment) |
| Q969J9 | Hypothetical protein (Similar to dystroglycan 1) |
| Q96AC3, Q96FV2, Q9BU04 | Hypothetical protein, Ses2 protein, Similar to KIAA0193 gene product (Fragment) |
| Q96B89, Q9H3J8, Q9HC37, Q9HC38, Q9Y3E8 | Hypothetical protein, My027 protein, Hypothetical protein, Hypothetical protein, CGI-150 protein |
| Q96B89, Q9H3J8, Q9HC37, Q9HC38, Q9Y3E8 | various names |
| Q96B89, Q9H3J8, Q9HC38, Q9Y3E8 | Hypothetical protein, My027 protein, Hypothetical protein, CGI-150 protein |
| Q96EI3, Q9H0W9 | Hypothetical protein |
| Q96NV4, Q9H0R4 | Hypothetical protein FLJ30028, Hypothetical protein |
| Q9H008 | Phospholysine phosphohistidine inorganic pyrophosphate phosphatase |
| Q9H2Y2, Q9NPH2, Q9NVW7 | Inositol 1-phosphate synthase, Myo-inositol 1-phosphate synthase A1, Hypothetical protein FLJ10463 |
| Q9NQ56, Q9NQ48 | Leucine zipper transcription factor-like 1 |
| Q9NX46 | DJ665N4.2 (Similar to hypothetical protein FLJ20446) (ADP-ribosyl-hydrolase precursor) |
| Q9Y5Z5, Q9NRV9 | Heme-binding protein, Heme-binding protein (Hypothetical protein) |
| Q9Y6R7 | Human Fc gamma BP (Fragment) |

Example 2

Introduction

Figure 5:
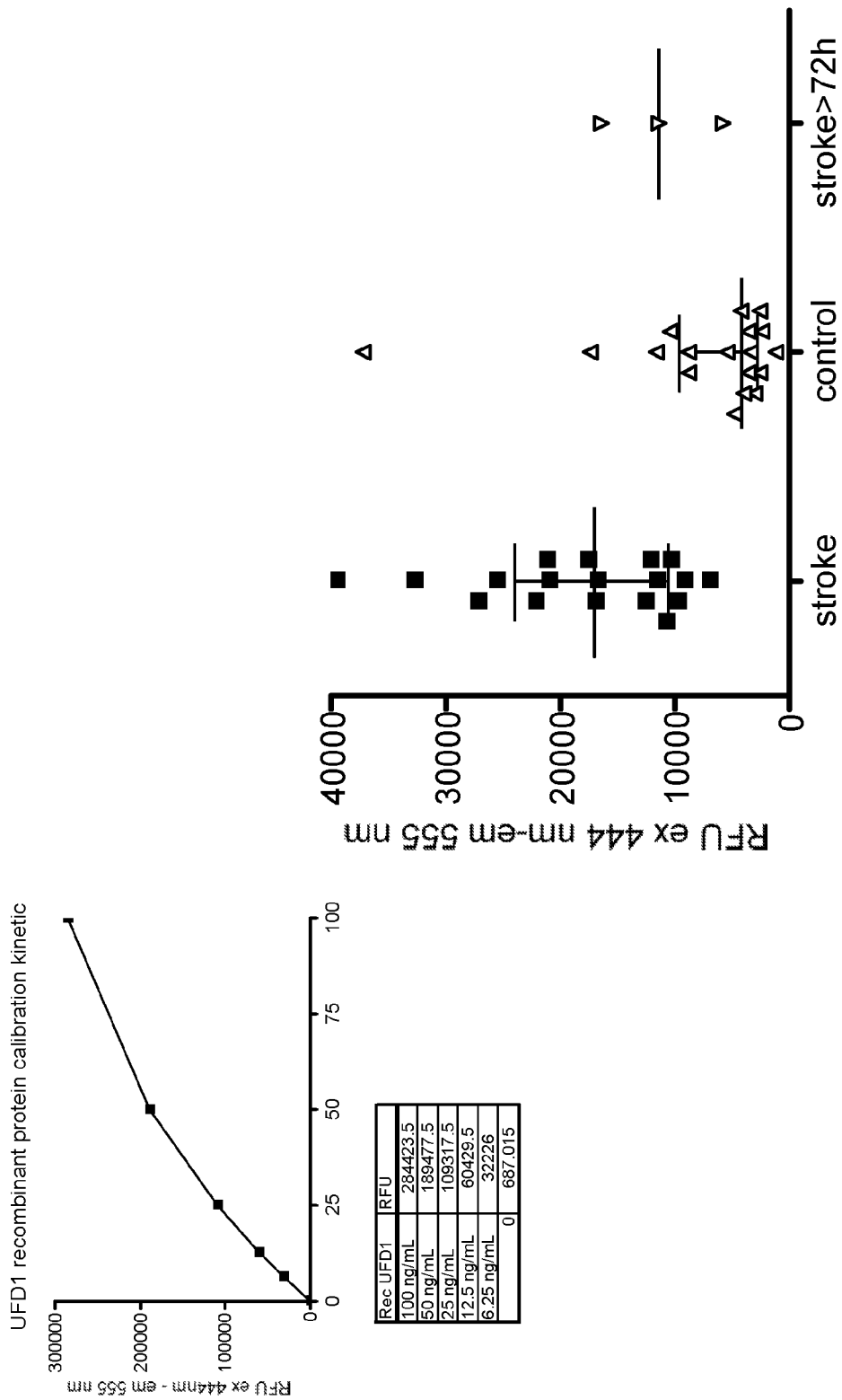
FIGS. 5-7 show results of an assay for UFD1 for two groups of patients: a control group and a group with acute stroke.
Figure 6:
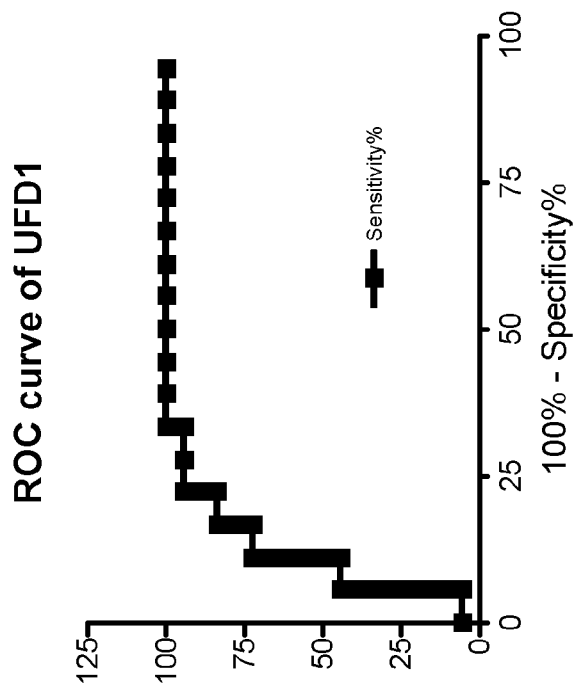
Figure 7:
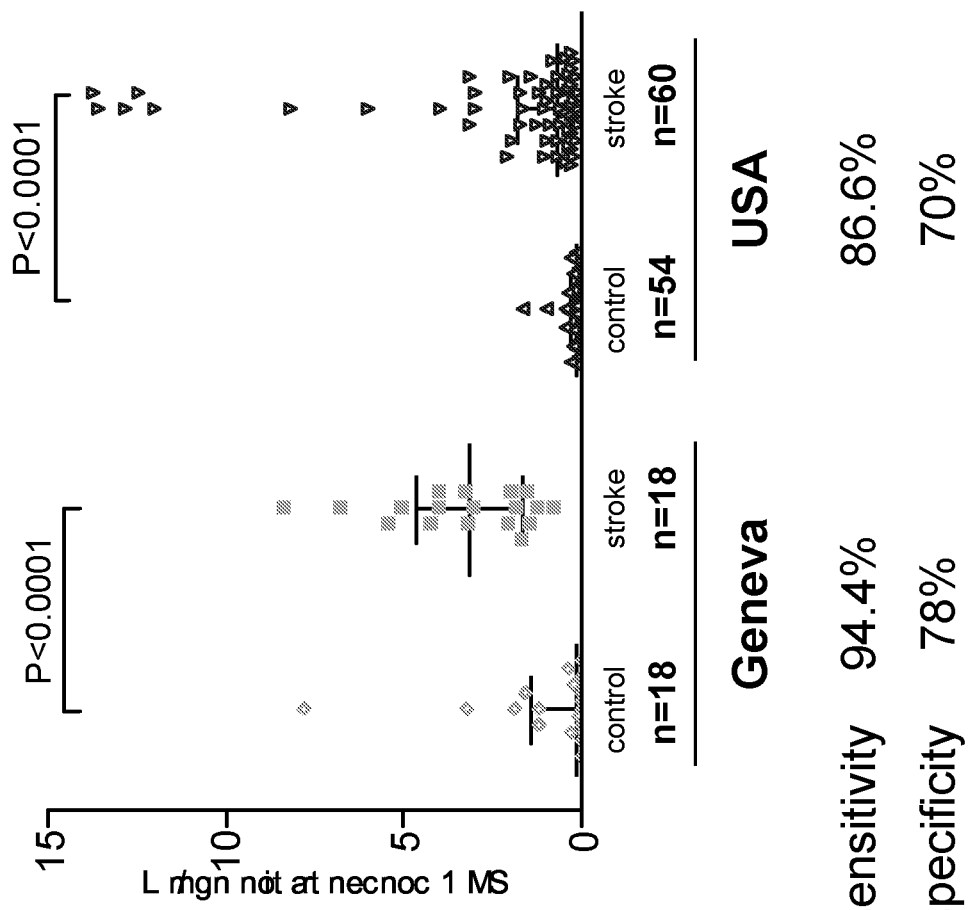

One of the proteins identified as being upregulated in deceased CSF was evaluated as a potential biomarker of cerebrovascular disease, an example of a brain damage-related disorder. A survey of stroke patients was carried out and the results are shown in FIGS. 5 to 7. An ELISA intensity signal was obtained for Ubiquitin fusion degradation protein 1 homolog (UFD1) in plasma samples of the patients and of negative control patients. Plasma samples were taken from patients between 0-24 hours and/or after 72 hours of arrival at emergency hospital, and were matched for age/sex with samples from control patients.

ELISA was performed using 96-well Reacti-Bind™ NeutrAvidin™ coated Black Plates (Pierce, Rockford, Ill.). Plates were first rinsed in Borate Buffer Saline pH 8.4 (BBS) (100 mM $H_3BO_3$, 25 mM $Na_2B_4O_7$ (Sigma, St Louis, Mo., USA), 75 mM NaCl (Merck, Darmastadt, Germany)) on a NOVAP-ATH™ washer (Bio-Rad, Hercules, Calif.). Then, 50 µl of biotin-conjugated antibody (2 µg/ml) prepared in the dilution buffer A at pH 7 (DB, Polyvinyl Alcohol, 80% hydrolyzed, Mol. Wt. 9000-10,000 (Aldrich, Milwaukee, Wis., USA), MOPS (3-[N-Morpholino] propane sulfonic acid) (Sigma), NaCl, $MgCl_2$ (Sigma), $ZnCl_2$ (Aldrich), pH6.90, BSA 30% Solution, Manufacturing Grade (Serological Proteins Inc., Kankakee, Ill.)), was added and incubated for one hour at 37° C. Plates were then washed 3 times in BBS in the plate washer. 50 µl of antigen was then added and incubated for one hour at 37° C. Recombinant proteins were diluted at 100, 50, 25, 12.5, 6.25 ng/ml in the dilution buffer A to establish a calibration curve. Plasma samples were diluted to the appropriate concentration in the dilution buffer A. After the washing step, 50 µl of alkaline phosphatase-conjugated antibody was added at the appropriate dilution in buffer A and incubated for one hour at 37° C. The 96-well plate was then washed 3 times with BBS in the plate washer and 50 µl of Attophos® AP Fluorescent substrate (Promega, Madison, Wis.) was added. Plates were read immediately on a SpectraMax GEMINI-XS fluorometer microtiter plate reader, (Molecular Devices Corporation, Sunnyvale, Calif., U.S.A.) ($\lambda_{excitation}$=444 nm and $\lambda_{emission}$=555 nm). Results are expressed in RFU and can be obtained in endpoint mode (only one reading) or in kinetic mode for 10 minutes. In kinetic mode, the plate reader was set to record using 6 flashes (per well) which were then integrated into an average. In this manner each well was analysed 6 times using a minimal interval time between each reading. This translated to a 2 minutes delay between readings. The slope was calculated and used to determine the final value for each well. The best cut-off value to discriminate between the control and the stroke (Ischemic plus hemorrhagic or Ischemic vs. Hemorrhagic) groups was determined using ROC curves generated in GraphPad Prism 4 software.

Conclusion

It is clear from FIG. 5 that UFD1 is overexpressed in the plasma of stroke patients compared to control patients. Statistical analysis was performed and ROC curves (GraphPad Prism 4 software) indicating sensitivity of the test as a function of 1-specificity (FIG. 6) were drawn. Best cutoff values to distinguish between stroke and control patients were deduced from these ROC curves. A sensitivity and specificity of 94.4% and 77.8%, respectively, was obtained using the best cutoff values. A non-parametric Mann-Whitney test was performed to compare stroke and control groups. Very low p values (<0.0001) were obtained, indicating that the difference between stroke and controls was highly significant.

This result demonstrates that Ubiquitin fusion degradation protein 1 homolog (UFD1) is a useful plasmatic marker for early diagnosis of stroke, alone, or in combination with other biomarkers.

As UFD1 has been found in deceased CSF, it is a reasonable prediction that other polypeptides and proteins differentially expressed in deceased CSF will also be useful as markers for brain damage-related disorders.

Example 3

This Example provides additional data showing plasma levels of UFDP1 in stroke and control patients. Additional data has been obtained from two cohorts of patients and controls, the smaller from Geneva, and a more comprehensive panel from the US.

ELISA was performed using 96-well Reacti-Bind™ NeutrAvidin™ coated Black Plates (Pierce, Rockford, Ill.). Plates were first rinsed in Borate Buffer Saline pH 8.4 (BBS) (100 mM H3BO3, 25 mM Na2B4O7 (Sigma, St Louis, Mo., USA), 75 mM NaCl (Merck, Darmastadt, Germany)) on a NOVAP-ATH™ washer (Bio-Rad, Hercules, Calif.). Then, 50 µl of relevant biomarker specific biotin-conjugated antibody (2 µg/mL) prepared in the dilution buffer A at pH 7 was added and incubated for one hour at 37° C. Plates were then washed 3 times in BBS in the plate washer. 50 µl of antigen or plasma was then added and incubated for one hour at 37° C. Recombinant protein antigens were diluted at 100, 50, 25, 12.5, 6.25, 3.125, 1.56 ng/ml in dilution buffer A to generate a calibration curve. Plasma samples were diluted to the appropriate concentration in dilution buffer A. After a further washing step, 50 µl of relevant biomarker specific alkaline phosphatase-conjugated antibodies was added at the appropriate concentration in dilution buffer A and incubated for one hour at 37° C. The 96-well plate was then washed 3 times with BBS in the plate washer and 50 µl of Attophos® AP Fluorescent substrate (Promega, Madison, Wis.) was added. Plates were read immediately on a SpectraMax GEMINI-XS fluorometer microtiter plate reader (Molecular Devices Corporation, Sunnyvale, Calif., U.S.A.) ($\lambda_{excitation}$=444 nm and $\lambda_{emission}$=555 nm).

Results are expressed in RFU and can be obtained in endpoint mode (only one reading) or in kinetic mode for 10 minutes. In kinetic mode, for each well 6 flashes were averaged and each well was analysed 6 times using a minimal interval time between each reading (2 minutes). The slope was calculated and used to determine the final value for each well. The best cut-off value to discriminate between the control and the stroke (Ischemic plus hemorrhagic or Ischemic vs. Hemorrhagic) groups was determined using ROC curves generated in GraphPad Prism 4 software.

The results are shown in FIG. 7. This result further demonstrates that Ubiquitin fusion degradation protein 1 homolog (UFD1) is a useful marker for early diagnosis of stroke, alone, or in combination with other biomarkers.

As UFD1 has been found in deceased CSF, it is a reasonable prediction that other polypeptides and proteins differentially expressed in deceased CSF will also be useful as markers for brain damage-related disorders.

Example 4

In the current work, we have used an alternative method to 2-DE in order to further characterize the human postmortem CSF proteome. A pool of postmortem CSF samples (n=5) was analyzed using a four step protocol: (i) immunodepletion of abundant CSF proteins (albumin, IgG, IgA, transferrin, antitrypsin, and haptoglobin), (ii) fractionation of CSF proteins according to their pI using off-gel electrophoresis (OGE) (24), (iii) analysis of fractions from OGE by SDS-PAGE, (iv) protein identification by LC-MS/MS. Selected proteins that were identified in postmortem CSF were validated using Western blots of individual postmortem and ante-mortem CSF samples. The potential interest of proteins identified in postmortem CSF as biomarkers of brain damage will be discussed.

Experimental Procedures

Materials:

All chemicals, unless otherwise stated, were purchased from Sigma Aldrich (St. Louis, Mich., USA) and were of the highest purity available. $CH_3CN$ was purchased from Biosolve (Westford, Mass., USA).

CSF Collection:

Postmortem CSF samples from five different patients were collected by ventricular puncture at autopsy, 6 hours after death on average. Deceased patients had no history, symptoms or signs of any psychiatric or neurological condition. Cause of death was unrelated to any dysfunction of the central or peripheral nervous system and neuropathological data of the brain were consistent with age-related changes with no relevant pathology. Control ante-mortem CSF samples were used for Western blot validation. They were collected by diagnostic lumbar puncture from five living patients who had a neurological workup for benign conditions unrelated to brain damage (atypical headache and idiopathic peripheral facial nerve palsy). Each patient or patient's relatives gave informed consent prior to enrolment. Atraumatic CSF samples were centrifuged immediately after collecting, aliquoted, frozen at −80° C., and stored until analysis.

Blood Sample Collection:

Plasma samples obtained from the Geneva University Hospital were used for the assessment of the level of GST-P1. The local institutional ethical committee board approved the clinical protocol. Seven consecutive stroke and control patients admitted to the Geneva University Hospital emergency unit were enrolled in this study. Of the 7 consecutive patients enrolled, 3 were diagnosed with non-neurological conditions and classified as control samples (2 men and 1 women, average age of 70.26 years) and 4 were diagnosed with stroke (3 men and 1 women, average age of 71.81 years) including 2 ischemic and 1 intra-cerebral hemorrhagic strokes. The diagnosis of stroke was established by a trained neurologist and was based on the sudden appearance of a focal neurological deficit and the subsequent delineation of a lesion consistent with the symptoms on brain CT or MRI images. The control group included patients with cancer (n=2) and a gastro-intestinal disorder (n=1). For each patient, a blood sample was collected at the time of admission in dry heparin-containing tubes within the three hours window after onset of symptoms. After centrifugation at 1500 g for 15 min at 4° C., samples were aliquoted and stored at −80° C. until analysis. Analyses were performed on frozen samples.

Depletion of Abundant Proteins:

Pooled postmortem CSF samples were concentrated to 300 µl using 10 kDa MWCO ultrafiltration devices (Vivaspin UF 4, Vivascience, Germany). The protein load was approximately 1.6 mg. The sample was then diluted 1:5 in MARS buffer A (Agilent, Palo Alto, Calif., USA) and passed through a 0.22 µm filter. Aliquots of 200 µl were injected on a 4.6×100 mm MARS column (Agilent). The flow-through fractions were collected, pooled and concentrated to approximately 1 ml using ultrafiltration. These concentrated fractions were washed twice with 10 mM $NH_4HCO_3$. A protein concentration assay was performed using the Bradford method (Bio-Rad, Hercules, Calif., USA).

Off-Gel Electrophoresis:

The OGE fractionation was performed as in Heller, M., Michel, P. E., Morier, P., Crettaz, D., Wenz, C., Tissot, J. D., Reymond, F., and Rossier, J. S. (2005) Two-stage Off-Gel isoelectric focusing: protein followed by peptide fractionation and application to proteome analysis of human plasma. *Electrophoresis* 26, 1174-1188. The depleted CSF was prepared for OGE by adding urea, thiourea and DTT to final concentrations of 7M, 2M and 65 mM, respectively. IPG strips (13 cm, pH 4.0-7.0) were rehydrated in a solution containing 7 M urea, 2 M thiourea, 65 mM DTT, 0.5% (v/v) ampholytes (pH 4.0-7.0) and 5% glycerol. A 15 well device was then placed on the rehydrated IPG and 50 µl of sample was loaded in each well across the whole strip. Several multiwell devices were used in parallel to allow fractionation of the whole sample in a single experiment. The voltage was started at 100 V (1 hour) then increased to 500 V (for 1 hour), 1000 V (for 1 hour) and finally to 2000 V where it was maintained for 15 hours. The focusing was performed at 20° C. with a current limit of 50 mA. Fractions were recovered from each of the wells.

SDS-PAGE and in-Gel Digestion:

Proteins from OGE fractions were separated by SDS-PAGE on home-made 12% T Tris-Glycine gels (8×5×0.15 cm). Approximately 60 µl of each fraction was loaded on the gel. After the migration, gels were stained with an MS-compatible silver stain (Blum, H., Beier, H., and Gross, H. J. (1987) Improved silver staining of plant proteins, RNA and DNA in polyacrylamide gels. *Electrophoresis* 8, 93-99). Bands cut from the silver-stained gels were destained with 15 mM $K_3Fe(CN_6)$, 50 mM $Na_2S_2O_3$, and washed with MilliQ water (Millipore, Billerica, Mass., USA) (26). The gel pieces were then dehydrated in 100% $CH_3CN$ and dried in a vacuum centrifuge. The proteins were in-gel digested using standard protocols (Scherl, A., Coute, Y., Deon, C., Calle, A., Kindbeiter, K., Sanchez, J. C., Greco, A., Hochstrasser, D., and Diaz, J. J. (2002) Functional proteomic analysis of human nucleolus. *Mol. Biol. Cell* 13, 4100-4109). Peptides were extracted with 1% TFA followed by 50% $CH_3CN$, 0.1% TFA. The combined extracts were concentrated by vacuum centrifugation.

LC-MS/MS:

Peptides extracted following in-gel digestion were dissolved in 9 µl 5% $CH_3CN$, 0.1% formic acid and 5 µl was loaded for LC-MS/MS analysis. A precolumn (100 µm inner diameter, 2-3.5 cm long) was connected directly to an analytical column (75 µm inner diameter, 9-10 cm long). Both columns were packed in-house with 5 µm, 3 Å Zorbax Extend C-18 (Agilent). A gradient from 4 to 56% solvent B in solvent A (Solvent A: 5% $CH_3CN$, 0.1% formic acid, Solvent B: 80% $CH_3CN$, 0.1% formic acid) was developed over 15 minutes at a flow rate of approximately 300 nl/min. The concentration of solvent B was increased to 95% before returning to start conditions for re-equilibration of the column. The eluate was sprayed directly into the nano-ESI source of an LCQ DecaXP ion trap mass spectrometer (Thermo Finnigan, San Jose, Calif.) with a spray voltage of 1.8-2.2 kV. Data dependent acquisition was used to automatically select 2 precursors for MS/MS from each MS spectrum (m/z range 400-1600). MS/MS spectra were acquired with a normalized collision energy of 35%, an activation Q of 0.25 and an isolation width of 4 m/z. The activation time was 30 milliseconds. Dynamic exclusion was applied with a repeat count of 2, an exclusion time of 30 seconds, and an exclusion peak width of ±1.5 Da. Wideband activation was also applied. Maximum injection times of 50 milliseconds and 200 milliseconds were used for MS and MS/MS acquisitions, respectively, and the corresponding automatic gain control targets were set to $10^8$.

Data Extraction and Database Interrogation:

Peak lists were generated using Bioworks 3.1 software (Thermo Finnigan, San Jose, Calif.). The resulting data files from each analysis were automatically combined into a single text file. The resulting peak lists were searched against the UniProt/Swiss-Prot database without species restriction using Mascot operating on a local server (version 1.8, Matrix Sciences, U.K.) and Phenyx Virtual Desktop (Gene Bio, Switzerland). Mascot was used with average mass selected, a precursor mass error of 2.0 Da and a peptide mass error of 1.0 Da. Trypsin was selected as the enzyme, with a single potential missed cleavage. ESI ion trap was selected as the instrument type and oxidized methionine as a variable modification. For Phenyx, ion trap was selected for the instrument type and LCQ for the algorithm. Two search rounds were used, both with trypsin selected as the enzyme and oxidized methionine as a variable modification. In the first round 1 missed cleavage was allowed and the normal cleavage mode was used. This round was selected in 'turbo' search mode. In the second round 2 missed cleavages were allowed and the cleavage mode was set to half-cleaved. The minimum peptide length allowed was 6 amino acids and the parent ion tolerance was 2.0 Da in both search rounds. The acceptance criteria were slightly lowered in the second round search (round 1: AC score 7.0, peptide Z-score 7.0, peptide p-value 1 E-6; round 2: AC score 7.0, peptide Z-score 6.0, peptide p-value 1 E-5).

Proteins that were identified as human proteins with 3 or more high-scoring peptides from both Mascot and Phenyx were accepted to be true matches. 'High scoring peptides' corresponded to peptides that were above the threshold in Mascot searches (5% probability of false match for each peptide above this score) and above a peptide score of 8.5 for Phenyx searches using the LCQ scoring algorithm. Matches with fewer than 3 peptides were manually validated. Single peptide matches were only included if they were high scoring peptides in the results from both programs and if the data was considered to match the peptide sequence well.

The peak lists were also searched against the UniProt combined Swiss-Prot and TrEMBL database restricted to human entries using Phenyx Virtual Desktop (Gene Bio, Switzerland). The acceptance criteria were more stringent than for the search of the Swiss Prot database alone (round 1: AC score 16.0, peptide Z-score 8.0, peptide p-value 1 E-7; round 2: AC score 10.0, peptide Z-score 7.0, peptide p-value 1 E-6).

Two-Dimensional Gel Electrophoresis:

A volume of 30 µl of crude or depleted CSF was mixed with 120 µl of a rehydration solution. The final solution contained 8M urea, 4% (w/v) CHAPS, 65 mM DTT, 2% (v/v) Resolytes 3.5-10 and a trace of bromophenol blue. The whole sample corresponding to approximately 6 µg of proteins was used for rehydration of a commercial 7 cm non-linear pH 3-10 IPG strip (GE Healthcare, Uppsala, Sweden). IEF was carried out. The second dimensional separation was performed on in-house manufactured SDS-PAGE gels (9×8×0.15 cm, 12% T, 2.6% C). Gels were then stained with ammoniacal silver.

Immunoblot Analyses of Ante- and Postmortem CSF Samples:

Postmortem and ante-mortem CSF samples (20 µl) were loaded on home-made 12% T Tris-Glycine gel (8×7×0.1 cm). The following positive controls were used: 100 ng of recombinant calcyphosine (Scientific Proteins, Switzerland), 100 ng of recombinant ubiquitin fusion degradation protein 1 (UFD1) (Biosite, San Diego, Calif., USA), 1 µl of U373 cell line extract for 14-3-3 protein isoform beta, and 5 µl of HeLa cell line extract for glutathione S-transferase P (GST-P). Proteins separated by SDS-PAGE were electroblotted onto a PVDF membrane as described by Towbin et al. (Towbin, H., Staehelin, T., and Gordon, J. (1979) Electrophoretic transfer of proteins from polyacrylamide gels to nitrocellulose sheets: procedure and some applications. *Proc. Natl. Acad. Sci. USA* 76, 4350-4354). Membranes were stained with Amido-Black, destained with water and dried. Immunodetection was performed using specific antibodies and BM Chemiluminescence Western Blotting Kit (Roche, Basel, Switzerland). The following antibodies were used: anti-human calcyphosine rabbit polyclonal antibody (Scientific Proteins, Witterswil, Switzerland) diluted 1/1000, anti-human UFD1 mouse Omniclonal® antibody (Biosite, San Diego, Calif., USA) diluted 1/1000, anti-human 14-3-3β rabbit polyclonal antibody (Santa Cruz Biotechnology, Santa Cruz, Calif., USA) diluted 1/500, anti-human GST-P mouse monoclonal antibody (Transduction Laboratories, Lexington, Ky., USA) diluted 1/1000.

Immunoblot Detection of 14-3-3 Protein in OGE Fractions:

Five µl of OGE fractions obtained from postmortem and ante-mortem CSF pools were loaded on home-made 12% T Tris-Glycine gels (8×7×0.1 cm). Five µl of crude postmortem and ante-mortem CSF pools were used as positive and negative controls, respectively. Proteins separated by 1-DE were electroblotted onto a PVDF membrane as described by Towbin et al. (30). Membranes were stained with Amido-Black, destained with water and dried. Immunodetection was performed using anti-human 14-3-3 rabbit polyclonal antibody (Santa Cruz Biotechnology, Santa Cruz, Calif., USA) diluted 1/500 and BM Chemiluminescence Western Blotting Kit (Roche, Basel, Switzerland).

Sandwich ELISA Detection of GST-P1:

As no commercial kit was available for the detection of GST-P1, a homemade ELISA test was developed. A trained laboratory technician carried out the assays (in an un-blind manner) with less than 15% coefficient variation. Sandwich ELISA was performed using 96-well Reacti-Bind™ NeutrAvidin™ coated Black Plates (Pierce, Rockford, Ill.). Plates were first rinsed in Borate Buffer Saline pH 8.4 (BBS) (100 mM $H_3BO_3$, 25 mM $Na_2B_4O_7$ (Sigma, St Louis, Mo., USA) 75 mM NaCl (Merck, Darmastadt, Germany)) on a NOVAP-ATH™ washer (Bio-Rad, Hercules, Calif.). Then, 50 µL of GST-P1 monoclonal antibody-biotin conjugated (2 µg/mL) prepared in the dilution buffer A at pH 7 (DB, Polyvinyl Alcohol, 80% hydrolyzed, Mol. Wt. 9000-10,000 (Aldrich, Milwaukee, Wis., USA), MOPS (Sigma), NaCl, $MgCl_2$ (Sigma), $ZnCl_2$ (Aldrich), pH6.90, BSA 30% Solution, Manufacturing Grade (Serological Proteins Inc., Kankakee, Ill.)), were added and incubated for one hour at 37° C. Plates were then washed 3 times in BBS in the plate washer. Fifty µL of blood or CSF samples were used diluted twice and incubated for one hour at 37° C. Each sample was assayed in duplicate and distributed randomly on the plate. Recombinant GST-P1 protein (Invitrogen,) was diluted at 100 ng/mL in the dilution buffer A. The calibration curve was performed in the same plate at a concentrations of 100, 50, 25, 12.5, 6.25, 3.125, 1.56 and 0 µg/L. After the washing step, 50 µL of alkaline phosphatase conjugated GST-P1 monoclonal antibodies were added at the appropriate dilution in the dilution buffer A and incubated for one hour at 37° C. The 96-well plate was then washed 3 times with BBS in the plate washer and 50 µL of fluorescence Attophos® AP Fluorescent substrate (Promega, Madison, Wis.) were added. Plates were read immediately on a SpectraMax GEMINI-XS, (Molecular Devices Corporation, Sunnyvale, Calif., U.S.A.) fluorometer microtiter plate reader using the endpoint mode relative fluorescence units (RFU) ($\lambda_{excitation}$=444 nm and $\lambda_{emission}$=555 nm). A calibration curve was performed using a linear regression in the linear range of the curve. Protein levels were initially expressed in relative fluorescence units (RFU) and the concentrations were calculated via the calibration curve.

Results:

Abundant Protein Depletion:

The analysis of body fluids, such as CSF, poses a challenge in terms of the high dynamic range of protein concentrations.

The dominance of particular proteins such as albumin and immunoglobulins results in many proteins of lower abundance remaining undetected by conventional techniques such as 2-DE and mass spectrometry. Therefore immunodepletion of some of the most abundant CSF proteins (albumin, serotransferrin, IgG, IgA, haptoglobin, and −1-antitrypsin) was performed in order to improve the coverage of low abundance proteins. To access the results from depletion of abundant proteins, 2-DE of the CSF samples was performed before and after immunoaffinity subtraction. The gels show major similarities before and after depletion and confirm that the removal of some abundant proteins enabled the detection of spots of lower abundance. This result obtained for the postmortem CSF sample reproduces perfectly those presented by Maccarrone et al. (Maccarrone, G., Milfay, D., Birg, I., Rosenhagen, M., Holsboer, F., Grimm, R., Bailey, J., Zolotarjova, N., and Turck, C. W. (2004) Mining the human cerebrospinal fluid proteome by immunodepletion and shotgun mass spectrometry. *Electrophoresis* 25, 2402-12) for ante-mortem CSF with similar depletion reproducibility from run to run (data not shown).

Figure 2:
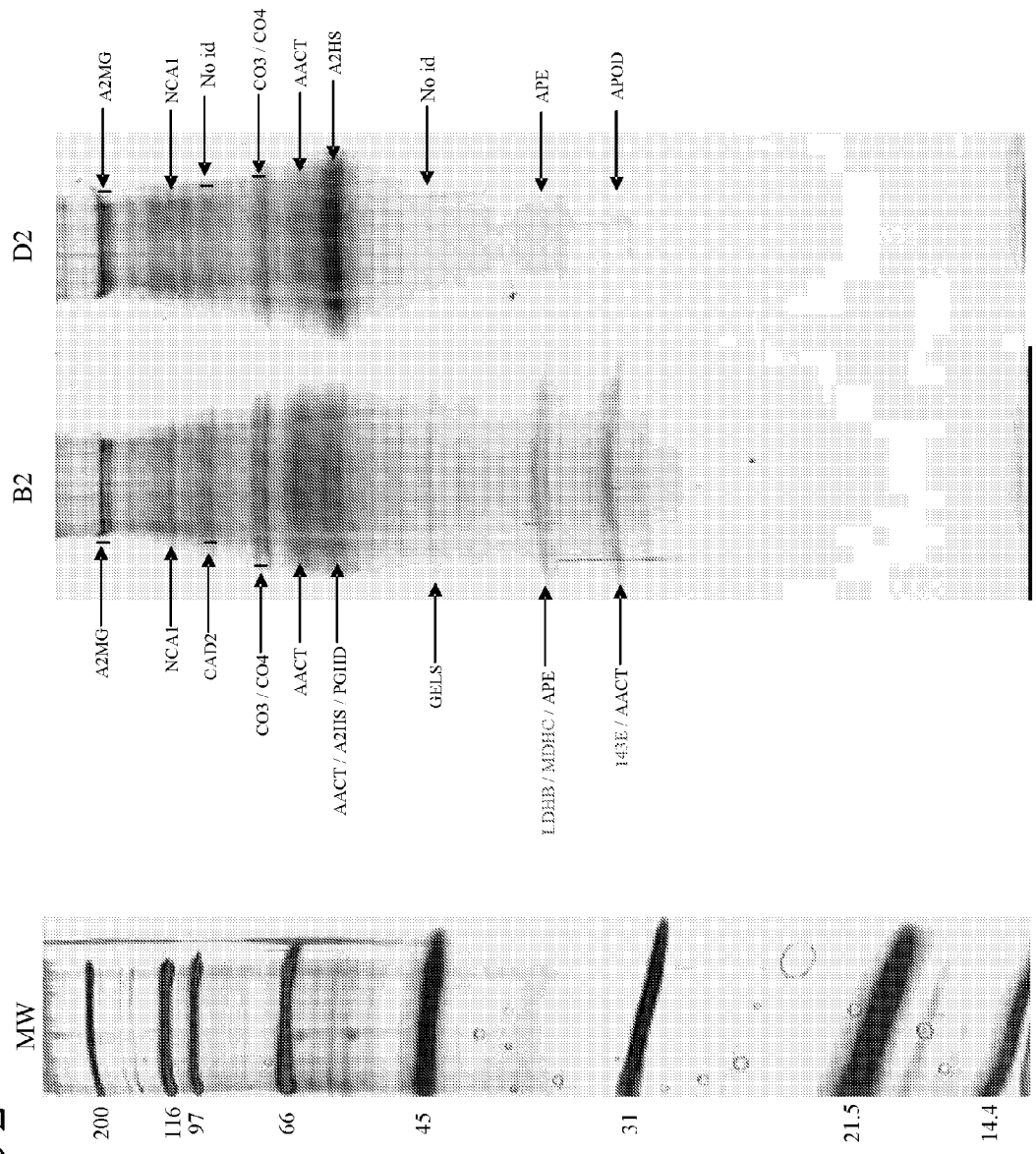
Figure 3:
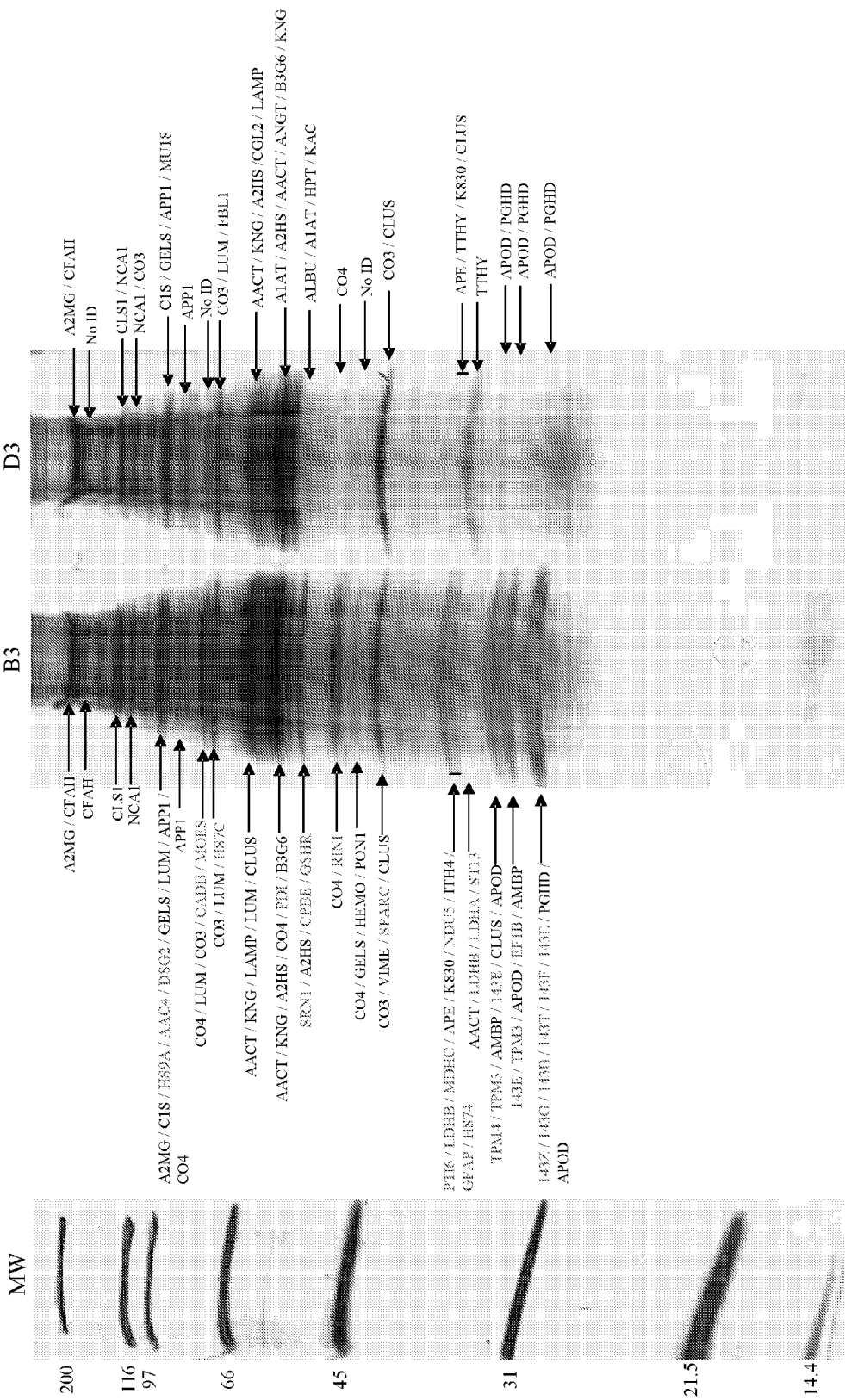
Figure 4:
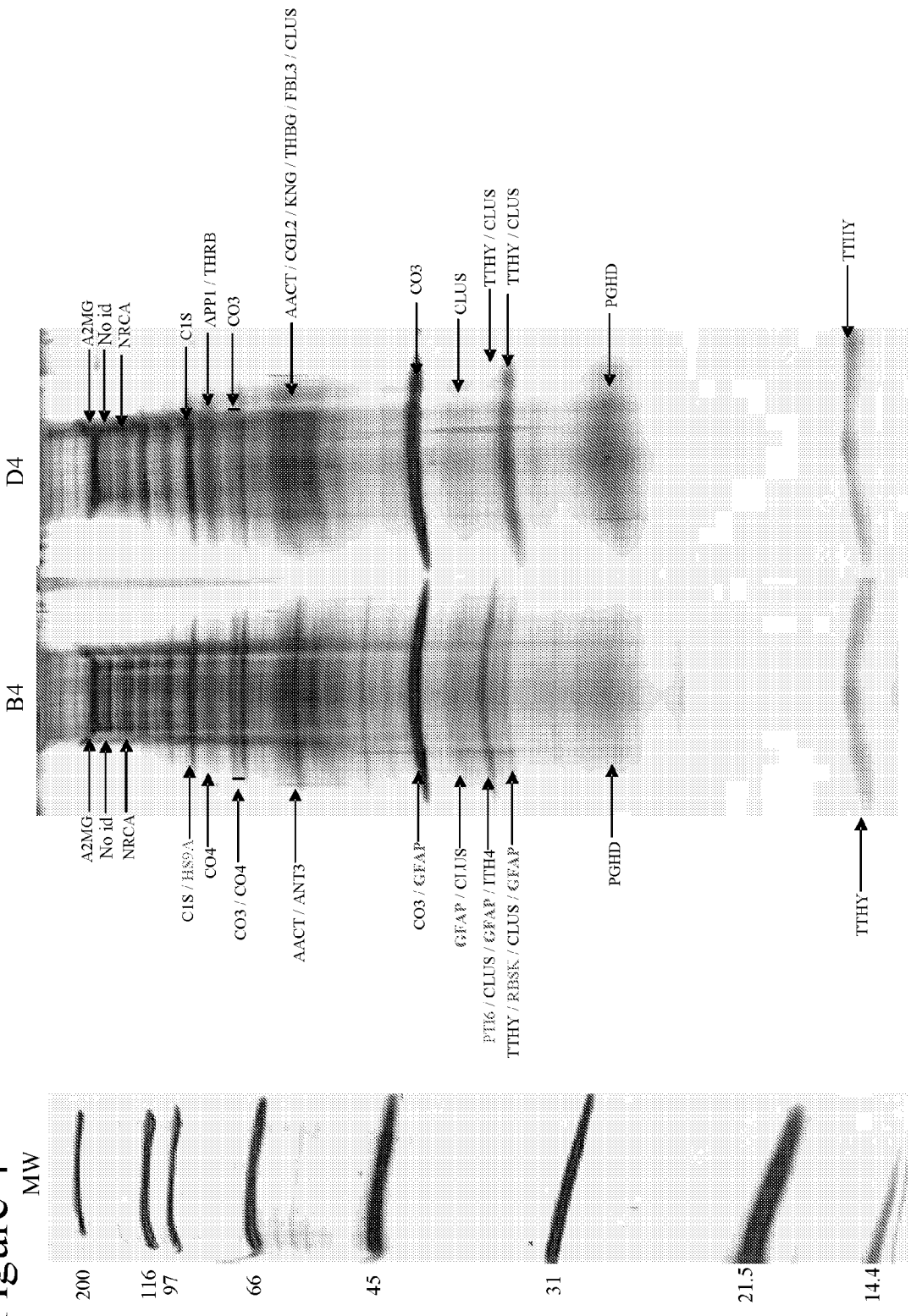

Off-Gel Electrophoresis:

Following depletion of abundant proteins, the postmortem CSF sample was fractionated by OGE according to their pI. OGE was performed using a pH gradient ranging from 4.0 to 7.0. The fractions obtained from OGE were then separated by SDS-PAGE. FIG. 2 shows a silver-stained SDS-PAGE gel of postmortem CSF sample. As a result of the OGE fractionation, with some bands were represented in multiple fractions and others concentrated in one or two fractions. Western blots were also used to verify the quality of the OGE fractionation.

A sample of the pooled postmortem CSF was separated by SDS-PAGE along with each of the fractions from OGE of the sample. For example, 14-3-3 protein gamma was apparent in the un-fractionated postmortem CSF sample and in a single fraction following OGE of the postmortem CSF sample (fraction 3). These results corresponded with the identifications obtained by MS and database searching. The 14-3-3 protein gamma was identified in one band of fraction 3 from the postmortem CSF fractionation (see Table 2). The ante-mortem CSF sample did not show any band for the gamma 14-3-3 protein.

Identification by Mass Spectrometry:

Proteins were identified from bands cut from the gels. Bands were cut from equivalent regions of both the postmortem CSF gels and the ante-mortem CSF gels. The only parts of the lanes that were not excised were those where neither the post-nor the ante-mortem samples showed bands. A total of 316 proteins were identified in this study and these results are listed in Tables 2 and 3, in which Table 2 contains proteins from the UniProt/Swiss-Prot database (searched with all species) and Table 3 contains proteins identified from the UniProt TrEMBL database (searched with the taxonomy restricted to human) (see Supplementary data). Of all the proteins identified, 294 were identified from the Swiss Prot database and a further 22 from the human TrEMBL searches. Of the 299 proteins that were identified from the postmortem CSF fractions, 201 were uniquely identified in postmortem CSF. A total of 115 proteins were identified in ante-mortem CSF fractions and 17 of these proteins were unique to these fractions. Of all the proteins identified, 98 were present in both the postmortem and ante-mortem CSF fractions.

TABLE 2

| | |
|---|---|
| O00241 | Signal-regulatory protein beta-1 |
| O00584 | *Ribonuclease* T2 |
| O14745 | Ezrin-radixin-moesin binding phosphoprotein 50 |
| O15394 | Neural cell adhesion molecule 2 |
| O43396 | Thioredoxin-like protein |
| O43488 | Aflatoxin B1 aldehyde reductase member 2 |
| O43505 | N-acetyllactosaminide beta-1,3-N-acetylglucosaminyltransferase |
| O43707 | Alpha-actinin 4 |
| O75223 | Protein C7orf24 |
| O94760 | NG,NG-dimethylarginine dimethylaminohydrolase 1 |
| O94919 | Probable Exonuclease KIAA0830 |
| O94985 | Calsyntenin-1 |
| O95336 | 6-phosphogluconolactonase |
| O95502 | Neuronal pentraxin receptor |
| O95861 | 3'(2'),5'-bisphosphate nucleotidase 1 |
| O95865 | NG,NG-dimethylarginine dimethylaminohydrolase 2 |
| P00352 | Retinal dehydrogenase 1 |
| P00390 | Glutathione reductase, mitochondrial |
| P00441 | Superoxide dismutase [Cu—Zn] |
| P00450 | Ceruloplasmin |
| P00491 | Purine nucleoside phosphorylase |
| P00734 | Prothrombin |
| P00738 | Haptoglobin |
| P00751 | Complement factor B |
| *P00915* | *Carbonic anhydrase I* |
| P00918 | Carbonic anhydrase 2 |
| P01008 | Antithrombin-III 130 |
| P01009 | Alpha-1-antitrypsin |
| P01011 | Alpha-1-antichymotrypsin |
| P01019 | Angiotensinogen |
| P01023 | Alpha-2-macroglobulin 1 |
| P01024 | Complement C3 |
| P01028 | Complement C4 |
| P01034 | Cystatin C |
| P01042 | Kininogen |
| P01834 | Ig kappa chain C region |
| P01857 | Ig gamma-1 chain C region |
| P01859 | Ig gamma-2 chain C |
| P01876, P01877 | Ig alpha-1 or -2 chain C region |

TABLE 2-continued

| | |
|---|---|
| P02545 | Lamin A/C (70 Kda lamin) |
| P02647 | Apolipoprotein A-I |
| P02649 | Apolipoprotein E |
| P02675 | Fibrinogen beta chain |
| P02679 | Fibrinogen gamma chain |
| P02741 | C-reactive protein |
| P02743 | Serum amyloid P-component |
| P02748 | Complement component C9 |
| P02751 | Beta-2-glycoprotein I |
| P02751 | Fibronectin |
| P02753 | Plasma retinol-binding protein |
| P02760 | AMBP protein |
| P02765 | Alpha-2-HS-glycoprotein |
| P02766 | Transthyretin |
| P02768 | Serum albumin |
| P02774 | Vitamin D-binding protein |
| P02787 | Serotransferrin |
| P02790 | Hemopexin |
| P02792 | Ferritin light chain |
| P02794 | Ferritin heavy chain |
| P04217 | Alpha-1B-glycoprotein |
| P04406 | Glyceraldehyde 3-phosphate dehydrogenase |
| P04746, P04745, P19961 | Alpha-amylase (Pancreatic, salivary or 2B) |
| P05089 | Arginase-1 |
| P05090 | Apolipoprotein D |
| P05156 | Complement factor I |
| P05216 | Tubulin alpha-6 chain |
| P05413 | Fatty acid-binding protein (H-FABP) |
| P05452 | Tetranectin |
| P05543 | Thyroxine-binding globulin |
| P05976 | Myosin light chain 1 |
| P06396 | Gelsolin |
| P06576 | ATP synthase beta chain |
| P06702 | Calgranulin B (MRP-14) |
| P06727 | Apolipoprotein A-IV |
| P06733 | Alpha enolase |
| P06753 | Tropomyosin alpha 3 chain |
| P07148 | Fatty acid-binding protein |
| P07195 | L-lactate dehydrogenase B chain |
| P07203 | Glutathione peroxidase 1 |
| P07225 | Vitamin K-dependent protein S |
| P07237 | Protein disulfide-isomerase |
| P07339 | Cathepsin D |
| P07357 | Complement component C8 alpha chain |
| P07738 | Bisphosphoglycerate mutase |
| P07900 | Heat shock protein HSP 90-alpha (HSP 86) |
| P07996 | Thrombospondin-1 |
| P08107 | Heat shock 70 kDa protein 1 |
| P08133 | Annexin A6 |
| P08238 | Heat shock protein HSP 90-beta (HSP 84) |
| P08294 | Extracellular superoxide dismutase [Cu—Zn] |
| P08571 | Monocyte differentiation antigen CD14 |
| P08603 | Complement factor H |
| P08670 | Vimentin |
| P08758 | Annexin A5 |
| P09211 | Glutathione S-transferase P |
| P09417 | Dihydropteridine reductase |
| P09486 | SPARC |
| P09488 | Glutathione S-transferase Mu 1 |
| P09493, P06753 | Tropomyosin 1 alpha chain or alpha 3 chain |
| P09525 | Annexin A4 |
| P09668 | Cathepsin H |
| P09871 | Complement C1s component |
| P09936 | Ubiquitin carboxyl-terminal hydrolase isozyme L1 |
| P09972 | Fructose-bisphosphate aldolase C |
| P10451 | Osteopontin |
| P10586 | Receptor-type tyrosine-protein phosphatase F |
| P10599 | Thioredoxin |
| P10643 | Complement component C7 |
| P10768 | Esterase D |
| P10909 | Clusterin |
| P11021 | 78 kDa glucose-regulated protein |
| P11142 | Heat shock cognate 71 kDa protein |
| P12277 | Creatine kinase, B chain |
| P12882 | Myosin heavy chain, skeletal muscle, adult 1 |
| P12883 | Myosin heavy chain, cardiac muscle beta isoform |
| P13489 | Placental ribonuclease inhibitor |
| P13535 | Myosin heavy chain, skeletal muscle, perinatal |
| P13592 | Neural cell adhesion molecule 1, 120 kDa isoform |
| P13611 | Versican core protein |

TABLE 2-continued

| | |
|---|---|
| P13693 | Translationally controlled tumor protein (TCTP) |
| P13716 | Delta-aminolevulinic acid dehydratase |
| P13929 | Beta enolase |
| P14136 | Glial fibrillary acidic protein, astrocyte (GFAP) |
| 550 | Alcohol dehydrogenase [NADP+] |
| P14618 | Pyruvate kinase, M1 isozyme |
| P14923 | Junction plakoglobin |
| P15090 | Fatty acid-binding protein, adipocyte (AFABP) |
| P15121 | Aldose reductase |
| P15259 | Phosphoglycerate mutase 2 |
| P15289 | Arylsulfatase A |
| P15311 | Ezrin |
| P15924 | Desmoplakin |
| P16035 | Metalloproteinase inhibitor 2 |
| P16083 | NRH dehydrogenase [quinone] 2 |
| P16870 | Carboxypeptidase H |
| P16930 | Fumarylacetoacetase |
| 04967 | Heat shock 70 kDa protein 6 |
| P17174 | Aspartate aminotransferase, cytoplasmic |
| P18206 | Vinculin (Metavinculin) |
| P18669 | Phosphoglycerate mutase 1 |
| P19022 | Neural-cadherin |
| P21266 | Glutathione S-transferase Mu 3 |
| P21333 | Filamin A |
| P21695 | Glycerol-3-phosphate dehydrogenase [NAD+] |
| P22061 | Protein-L-isoaspartate(D-aspartate) O-methyltransferase |
| P22314 | Ubiquitin-activating enzyme E1 |
| P23141 | Liver carboxylesterase 1 |
| P23142 | Fibulin-1 |
| P23528 | Cofilin, non-muscle isoform |
| P24534 | Elongation factor 1-beta |
| P24592 | Insulin-like growth factor binding protein 6 |
| P25786 | Proteasome subunit alpha type 1 |
| P25788 | Proteasome subunit alpha type 3 |
| P26041 | Moesin |
| P26641 | Elongation factor 1-gamma |
| P27169 | Serum paraoxonase/arylesterase 1 |
| P27348 | 14-3-3 protein tau |
| P28072 | Proteasome subunit beta type 6 |
| P28161 | Glutathione S-transferase Mu 2 |
| P28827 | Receptor-type protein-tyrosine phosphatase mu |
| P29218 | Inositol-1(or 4)-monophosphatase |
| P29401 | Transketolase |
| P30040 | Endoplasmic reticulum protein ERp29 |
| P30041 | Peroxiredoxin 6 |
| P30044 | Peroxiredoxin 5, mitochondrial |
| P30086 | Phosphatidylethanolamine-binding protein (PEBP) |
| P30101 | Protein disulfide-isomerase A3 |
| P30626 | Sorcin |
| P30740 | Leukocyte elastase inhibitor (LEI) |
| P31150 | Rab GDP dissociation inhibitor alpha |
| P31947 | 14-3-3 protein beta/alpha |
| P31948 | Stress-induced-phosphoprotein 1 |
| P32119 | Peroxiredoxin 2 |
| P34932 | Heat shock 70 kDa protein 4 |
| P35080 | Profilin-2 |
| P35237 | Placental thrombin inhibitor |
| P36955 | Pigment epithelium-derived factor |
| P36980 | Complement factor H-related protein 2 |
| P37837 | Transaldolase |
| P40121 | Macrophage capping protein |
| P40925 | Malate dehydrogenase, cytoplasmic |
| P41222 | Prostaglandin-H2 D-isomerase |
| P42126 | 3,2-trans-enoyl-CoA isomerase, mitochondrial |
| P43652 | Afamin |
| P45381 | Aspartoacylase |
| P46940 | Ras GTPase-activating-like protein IQGAP1 |
| P47756 | F-actin capping protein beta subunit |
| P48637 | Glutathione synthetase |
| P49419 | Aldehyde dehydrogenase family 7 member A1 |
| P50135 | Histamine N-methyltransferase |
| P50395 | Rab GDP dissociation inhibitor beta |
| P51693 | Amyloid-like protein 1 |
| P51884 | Lumican |
| P52565 | Rho GDP-dissociation inhibitor 1 |
| P52566 | Rho GDP-dissociation inhibitor 2 |
| P52907 | F-actin capping protein alpha-1 subunit |
| P54289 | Dihydropyridine-sensitive L-type, calcium channel alpha-2/delta subunits |
| P54652 | Heat shock-related 70 kDa protein 2 |

TABLE 2-continued

| | |
|---|---|
| P54764 | Ephrin type-A receptor 4 |
| *P54922* | *ADP-ribosylarginine hydrolase* |
| P55287 | Cadherin-11 |
| P55855 | Ubiquitin-like protein SMT 3A or 3B |
| P57087 | Junctional adhesion molecule 2 |
| P60174 | Triosephosphate isomerase |
| P60709 | Actin, cytoplasmic 1 |
| P60900 | Proteasome subunit alpha type 6 |
| P61088 | Ubiquitin-conjugating enzyme E2 N |
| P61917 | Epididymal secretory protein E1 |
| P61981 | 14-3-3 protein gamma |
| P62258 | 14-3-3 protein epsilon |
| P62941 | Peptidyl-prolyl cis-trans isomerase A |
| P62988 | Ubiquitin |
| P87379 | Growth factor receptor-bound protein 2 |
| P63103 | 14-3-3 protein zeta/delta |
| P63261 | Actin, cytoplasmic 2 |
| P67936 | Tropomyosin alpha 4 chain |
| P68136 | Actin, alpha skeletal muscle |
| P68224 | Hemoglobin beta chain |
| P78324 | Tyrosine-protein phosphatase non-receptor type substrate 1 |
| P78417 | Glutathione transferase omega 1 |
| P81605 | Dermcidin |
| P98160 | Basement membrane-specific heparan sulfate proteoglycan core protein |
| Q00169 | Phosphatidylinositol transfer protein alpha isoform |
| Q01082 | Spectrin beta chain, brain 1 |
| Q01469 | Fatty acid-binding protein, epidermal (E-FABP) |
| Q01995 | Transgelin |
| Q03591 | Complement factor H-related protein 1 |
| Q02246 | Contactin-2 |
| Q04917 | 14-3-3 protein eta |
| Q06033 | Inter-alpha-trypsin inhibitor heavy chain H3 |
| Q06830 | Peroxiredoxin 1 |
| Q12765 | Secernin 1 |
| Q12860 | Contactin 1 |
| Q13228 | Selenium-binding protein 1 |
| Q13332 | Receptor-type tyrosine-protein phosphatase S |
| Q13449 | Limbic system-associated membrane protein |
| Q13509 | Tubulin beta-4 |
| Q13740 | CD166 antigen |
| Q13813 | Spectrin alpha chain, brain |
| Q14118 | Dystroglycan |
| Q14126 | Desmoglein 2 |
| Q14515 | SPARC-like protein 1 |
| Q14624 | Inter-alpha-trypsin inhibitor heavy chain H4 |
| Q15818 | Neuronal pentraxin I |
| Q15149 | Plectin 1 |
| Q15181 | Inorganic pyrophosphatase |
| Q16270 | Insulin-like growth factor binding protein 7 |
| Q16555 | Dihydropyrimidinase related protein-2 |
| Q16620 | BDNF/NT-3 growth factors receptor |
| Q16881 | Thioredoxin reductase 1, cytoplasmic |
| Q86UP2 | Kinectin |
| Q86YZ3 | Hornerin |
| Q8N0Y7 | Putative phosphoglycerate mutase 3 |
| Q8TAG5 | Immunoglobulin-like domain protein MGC33530 |
| Q8TD26 | Chromodomain-helicase-DNA-binding protein 6 |
| Q92520 | Protein FAM3C |
| Q92598 | Heat-shock protein 105 kDa |
| Q92823 | Neuronal cell adhesion molecule |
| Q92876 | Kallikrein-6 |
| Q92890 | Ubiquitin fusion degradation protein 1 homolog |
| Q969H8 | Protein C19 or f10 |
| Q96IU4 | CCG1-interacting factor B |
| Q96KN2 | Glutamate carboxypeptidase-like protein 2 |
| Q96NY7 | Chloride intracellular channel 6 |
| Q99497 | DJ-1 protein |
| Q9BX68 | Histidine triad nucleotide-binding protein 2 |
| Q9H477 | Ribokinase |
| Q9NVS9 | Pyridoxine-5'-phosphate oxidase |
| Q9NZT1 | Calmodulin-like protein 5 |
| Q9P0L0 | Vesicle-associated membrane protein-associated protein A |
| Q9P121 | Neurotrimin |
| Q9P1W8 | Signal-regulatory protein beta-2 |
| *Q9P2S2* | *Neurexin 2-alpha* |
| Q9UBP4 | Dickkopf related protein-3 |
| Q9UBQ7 | Glyoxylate reductase/hydroxypyruvate reductase |
| Q9UKK9 | ADP-sugar pyrophosphatase |
| Q9UKX2 | Myosin heavy chain, skeletal muscle, adult 2 |

TABLE 2-continued

| | |
|---|---|
| Q9UN36 | NDRG2 protein |
| Q9Y617 | Phosphoserine aminotransferase |
| Q9Y623 | Myosin heavy chain, skeletal muscle, fetal |
| | TrEMBL entries |
| O00533 | Neural cell adhesion molecule |
| O43598 | RCL (Similar to putative C-MYC-responsive) |
| O95784 | IgG Fc binding protein (Fragment) |
| Q07898, Q07899, Q07900, Q07901, Q86VB7 | M130 antigen; M130 antigen cytoplasmic variant 1; variant 2; M130 antigen extracellular variant; Similar to CD163 antigen |
| Q7Z664 | Hypothetical protein DKFZp779N0926 (Fragment) |
| Q7Z7P9 | Hypothetical protein |
| Q8IZY7 | Hepatocellular carcinoma associated protein TB6 |
| Q8N240 | Hypothetical protein FLJ34957 |
| Q8NCW5 | ApoA-I binding protein |
| Q8NFZ8 | TSLC1-like 2 |
| Q96AC3, Q96FV2, Q9BU04, Q96B89, Q9H3J8, Q9HC37, Q9HC38, Q9Y3E8 | Hypothetical protein, Ses2 protein, Similar to KIAA0193 gene product (Fragment) Hypothetical protein, My027 protein, Hypothetical protein, Hypothetical protein, CGI-150 protein |
| Q96EI3, Q9H0W9 | Hypothetical protein |
| Q96NV4, Q9H0R4 | Hypothetical protein FLJ30028 |
| Q9H008 | Phospholysine phosphohistidine inorganic pyrophosphate phosphatase |
| Q9H2Y2, Q9NPH2, Q9NVW7 | Inositol 1-phosphate synthase; Myo-inositol 1-phosphate synthase A1; Hypothetical protein FLJ10463 |
| Q9NQ56, Q9NQ48 | Leucine zipper transcription factor-like 1 |
| Q9NX46 DJ665N4.2 | (Similar to hypothetical protein FLJ20446) (ADP-ribosyl-hydrolase precursor) |
| Q9Y5Z5, Q9NRV9 | Heme-binding protein (Hypothetical protein) |
| Q9Y6R7 | Human Fc gamma BP (Fragment) |

Entries in regular letters indicates Phenyx software results
These proteins were identified both with Phenyx and MASCOT softwares
Entries in italic indicates Phenyx software results
These proteins were identified only with Phenyx software
Entries in italic and bold indicates MASCOT software results
These proteins were identified only with MASCOT software

TABLE 3

| UniProt Accession number | Protein name | Identified in the following post-mortem fractions[a] | Previously identified in CSF in the following references |
|---|---|---|---|
| O00241 | Signal-regulatory protein beta-1 | 14 | |
| O00533 | Neural cell adhesion molecule | 4 5, 7, 9 | 14, 13, 15 |
| O00584 | Ribonuclease T2 | 5 | 15 |
| O14745 | Ezrin-radixin-moesin binding phosphoprotein 50 | 5, 6, 7, 8 | 13 |
| O15394 | Neural cell adhesion molecule 2 | 8 | |
| O43396 | Thioredoxin-like protein 1 | 5 | |
| O43488 | Aflatoxin B1 aldehyde reductase member 2 | 12, 14, 15 | |
| O43505 | N-acetyllactosaminide beta-1,3-N-acetylglucosaminyltransferase | 3, 5, 6, 7, 8, 10 | 7, 9, 14, 13, 15 |
| O43598 | RCL (Similar to putative C-MYC-responsive) | 5 | |
| O43707 | Alpha-actinin 4 | 3, 5, 7, 8 | |
| O75223 | Protein C7orf24 | 5 | |
| O94760 | NG,NG-dimethylarginine dimethylaminohydrolase 1 | 6, 7, 8, 9 | 13 |
| O94919 | Probable Exonuclease KIAA0830 | 3 | |
| O94985 | Calsyntenin-1 | 3 | 15 |
| O95336 | 6-phosphogluconolactonase | 6, 8, 10, 11 | |
| O95502 | Neuronal pentraxin receptor | 6, | 14, 13, 15 |
| O95784 | IgG Fc binding protein (Fragment) | 7 | |
| O95861 | 3'(2'),5'-bisphosphate nucleotidase 1 | 8 | |

TABLE 3-continued

| UniProt Accession number | Protein name | Identified in the following post-mortem fractions[a] | Previously identified in CSF in the following references |
|---|---|---|---|
| O95865 | NG,NG-dimethylarginine dimethylaminohydrolase 2 | 10 | 13 |
| P00352 | Retinal dehydrogenase 1 | 14, 15 | |
| P00390 | Glutathione reductase, mitochondrial | 3 | |
| P00441 | Superoxide dismutase [Cu—Zn] | 8, 9, 10, 12 | 7, 9, 14 |
| P00450 | Ceruloplasmin | 5, 6, 7, 8, 9 | 4, 7, 9, 14, 13, 15 |
| P00491 | Purine nucleoside phosphorylase | 14, 15 | |
| P00734 | Prothrombin | 5 | 9, 14, 13, 5, 15 |
| P00738 | Haptoglobin | 8 | 7, 9, 13, 15 |
| P00751 | Complement factor B | 12, 14 | 9, 15 |
| P00915 | Carbonic anhydrase I | 14, 15 | 10 |
| P00918 | Carbonic anhydrase II | 11, 12, 13, 14, 15 | 13 |
| P01008 | Antithrombin-III | 4, 5, 6, 7 | 9, 13, 15 |
| P01009 | Alpha-1-antitrypsin | 8 | 4, 7, 9, 14, 13 |
| P01011 | Alpha-1-antichymotrypsin | 1, 2, 3, 4, 5 | 4, 7, 9, 14 |
| P01019 | Angiotensinogen | 5, 6, 7, 8, 9, 10 | 9, 14, 13, 15 |
| P01023 | Alpha-2-macroglobulin | 2, 3, 4, 5, 7, 8, 9, 11, 12, 13, 14 | 4, 7, 14, 15 |
| P01024 | Complement C3 | 1, 2, 3, 4, 5, 6, 7, 8, 9, 10, 11, 12, 13, 14, 15 | 7, 9, 14, 13, 15 |
| P01028 | Complement C4 | 2, 3, 4, 5, 6, 7, 8, 9, 12, 13, 14, 15 | 7, 9, 14, 13, 5, 15 |
| P01034 | Cystatin C | 12, 15 | 4, 7, 9, 13, 5, 15 |
| P01042 | Kininogen | 3 | 9, 15 |
| P01834 | Ig kappa chain C region | 5, 8, 11 | 7, 5, 15 |
| P01857 | Ig gamma-1 chain C region | 8, 11 | 4, 7, 9, 5, 15 |
| P01859 | Ig gamma-2 chain C region* | 8 | 7 |
| P01876, P01877 | Ig alpha-1 or -2 chain C region | 5, 8, 11 | |
| P02545 | Lamin A/C (70 kDa lamin) | 14 | |
| P02647 | Apolipoprotein A-I | 5, 6, 7, 8 | 4, 7, 9, 14, 13, 15 |
| P02649 | Apolipoprotein E | 1, 2, 3, 5, 6, 7, 8, 9, 10, 12, 14 | 4, 7, 9, 13, 5, 15 |
| P02675 | Fibrinogen beta chain | 8, 10, 11, 12, 13, 14 | 7, 9, 15 |
| P02679 | Fibrinogen gamma chain | 6, 7, 8, 9, 10, 11, 12 | 7, 9, 14, 15 |
| P02741 | C-reactive protein | 6 | |
| P02743 | Serum amyloid P-component | 9 | 9 |
| P02748 | Complement component C9 | 5, 6 | |
| P02749 | Beta-2-glycoprotein I (Apolipoprotein H) | 12, 14, 15 | 9, 15 |
| P02751 | Fibronectin | 5, 7, 8, 9 | 9, 14, 13, 15 |
| P02753 | Plasma retinol-binding protein | 6, 7 | 7, 9, 13, 15 |
| P02760 | AMBP protein | 3, 5 | 4, 9, 5 |
| P02765 | Alpha-2-HS-glycoprotein | 2, 3 | 9, 14, 15 |
| P02766 | Transthyretin | 4, 5, 6, 7, 8, 9, 10, 11 | 4, 7, 9, 14, 13, 5, 15 |
| P02768 | Serum albumin | 5, 8, 9 | 4, 7, 9, 5, 15 |
| P02774 | Vitamin D-binding protein | 5, 6, 7 | 7, 9, 14, 13, 5, 15 |
| P02787 | Serotransferrin | 8 | 4, 7, 9, 13, 15 |
| P02790 | Hemopexin | 3, 5, 6, 7, 8, 9, 10, 11, 14 | 4, 9, 14, 13, 15 |
| P02792 | Ferritin light chain | 5, 6, 7, 8, 9 | 13 |
| P02794 | Ferritin heavy chain | 5, 6, 7 | 13 |
| P04217 | Alpha-1B-glycoprotein | 5, 6, 7 | 9, 14, 15 |
| P04406 | Glyceraldehyde-3-phosphate dehydrogenase, liver | 9 | 7, 13, 10 |
| P04746, P04745, P19961 | Alpha-amylase (pancreatic, salivary or 2B) | 5 | |
| P05089 | Arginase 1 | 15 | |
| P05090 | Apolipoprotein D | 3 | 4, 7, 15 |
| P05156 | Complement factor I | 5, 8, 9 | 7, 15 |
| P05209, Q9BQE3 | Tubulin alpha-1 or alpha-6 chain | 5, 6 | |
| P05413 | Fatty acid-binding protein, heart (H-FABP) | 12 | |
| P05452 | Tetranectin | 6, 8, 9 | 7, 9, 15 |
| P05543 | Thyroxine-binding globulin | 5, 6 | |

TABLE 3-continued

| UniProt Accession number | Protein name | Identified in the following post-mortem fractions[a] | Previously identified in CSF in the following references |
|---|---|---|---|
| P05976 or P06741 | myosin light chain 1 or 3, skeletal muscle isoform | 9 | |
| P06396 | Gelsolin | 2, 3, 5, 6, 8, 9, 10, 11, 12, 14, 15 | 4, 7, 9, 14, 13, 5, 15 |
| P06576 | ATP synthase beta chain, mitochondrial | 5 | |
| P06702 | Calgranulin B (MRP-14) | 9 | |
| P06727 | Apolipoprotein A-IV | 5, 6 | 4, 7, 9, 13, 5, 15 |
| P06733 | Alpha enolase | 10, 11, 12, 13, 14, 15 | 13, 10 |
| P06753 | Tropomyosin alpha 3 chain | 3 | |
| P07148 | Fatty acid-binding protein, liver (L-FABP) | 12 | |
| P07195 | L-lactate dehydrogenase B chain | 1, 2, 3, 5, 7, 8, 9, 10, 11, 12 | 7, 13 |
| P07203 | Glutathione peroxidase 1 | 10, 12 | |
| P07225 | Vitamin K-dependent protein S | 5 | |
| P07237 | Protein disulphide-isomerase | 3 | |
| P07339 | Cathepsin D | 6, 7, 8, 9, 10 | 9, 13 |
| P07357 | Complement C8 alpha chain | 10 | |
| P07738 | Bisphosphoglycerate mutase | 10 | |
| P07900 | Heat shock protein HSP 90-alpha (HSP 86) | 3, 4, 5, 6 | |
| P07996 | Thrombospondin 1 | 14 | |
| P08107 | Heat shock 70 kDa protein 1 | 7, 8, 9, 10 | 13 |
| P08133 | Annexin A6 | 8, 9 | |
| P08238 | Heat shock protein HSP 90-beta (HSP 84) (HSP 90) | 5 | 13 |
| P08294 | Extracellular superoxide dismutase [Cu—Zn] | 5, 6, 9, 10, 11, 12, 13, 14, 15 | 7, 13, 15 |
| P08571 | Monocyte differentiation antigen CD14 | 5, 6, 7, 8 | 9, 13, 15 |
| P08603 | Complement factor H | 8, 9, 12 | 9, 15 |
| P08670 | Vimentin | 3 | 13 |
| P08758 | Annexin A5 | 5 | |
| P09211 | Glutathione S-transferase P | 5, 6, 7, 8, 9, 11 | 13 |
| P09417 | Dihydropteridine reductase | 14 | |
| P09486 | SPARC | 3 | 13, 15 |
| P09488 | Glutathione S-transferase Mu 1 | 13, 14 | |
| P09493 or P06753 | Tropomyosin 1 alpha chain or alpha 3 chain | 9 | |
| P09525 | Annexin A4 | 10 | |
| P09668 | Cathepsin H | 9, 11 | |
| P09871 | Complement C1s subcomponent | 3 | |
| P09936 | Ubiquitin carboxyl-terminal hydrolase isozyme L1 | 6, 7, 8 | 15 |
| P09972 | Fructose-bisphosphate aldolase C | 12, 13, 14, 15 | 13 |
| P10451 | Osteopontin | 5 | 14, 13, 15 |
| P10586 | Receptor-type tyrosine-protein phosphatase F | 8 | |
| P10599 | Thioredoxin | 5 | |
| P10643 | Complement component C7 | 12 | 15 |
| P10768 | Esterase D | 14 | |
| P10909 | Clusterin | 3, 4, 5, 6, 7, 8, 9, 10, 11, 12 | 4, 7, 9, 13, 15 |
| P11021 | 78 kDa glucose-regulated protein | 5 | |
| P11142 | Heat shock cognate 71 kDa protein | 3, 6, 7, 8, 9, 14 | 15 |
| P12277 | Creatine kinase, B chain | 6, 7, 8, 9 | 13 |
| P12882 | Myosin heavy chain, skeletal muscle, adult 1 | 9 | 7 |
| P12883 | Myosin heavy chain, cardiac muscle beta isoform | 8 | |
| P13489 | Placental ribonuclease inhibitor | 3 | |
| P13535 | Myosin heavy chain, skeletal muscle, perinatal | 9 | |
| P13591, P13592 | Neural cell adhesion molecule 1, 140 kDa isoform or 120 kDa isoform | 2, 3 | |
| P13611 | Versican core protein | 3 | |
| P13693 | Translationally controlled tumor protein (TCTP) | 4 | |
| P13716 | Delta-aminolevulinic acid dehydratase | 14, 15 | |
| P13929 | Beta enolase | 14 | |
| P14136 | Glial fibrillary acidic protein, astrocyte (GFAP) | 3, 4, 5 | 4 |
| P14550 | Alcohol dehydrogenase [NADP+] | 14, 15 | |
| P14618 | Pyruvate kinase, isozymes M1/M2 | 5 | 13, 15 |
| P14923 | Junction plakoglobin | 15 | |
| P15090 | Fatty acid-binding protein, adipocyte (AFABP) | 12 | |
| P15121 | Aldose reductase | 14, 15 | 10 |

TABLE 3-continued

| UniProt Accession number | Protein name | Identified in the following post-mortem fractions[a] | Previously identified in CSF in the following references |
|---|---|---|---|
| P15259 | Phosphoglycerate mutase 2 | 10 | |
| P15289 | Arylsulfatase A | 9 | |
| P15311 | Ezrin | 3, 5, 12 | 13 |
| P15924 | Desmoplakin | 15 | |
| P16035 | Metalloproteinase inhibitor 2 | 14 | 15 |
| P16083 | NRH dehydrogenase [quinone] 2 | 11 | 13 |
| P16870 | Carboxypeptidase E | 3, 5, 6 | 13, 15 |
| P16930 | Fumarylacetoacetase | 14 | |
| P17066 | Heat shock 70 kDa protein 6 | 5, 8, 9, 10, 13 | |
| P17174 | Aspartate aminotransferase, cytoplasmic | 14, 15 | 13, 10 |
| P18206 | Vinculin | 8 | |
| P18669 | Phosphoglycerate mutase 1 | 10, 11, 12, 13, 14, 15 | 13 |
| P19022 | Neural-cadherin | 2, 5 | 13, 15 |
| P21266 | Glutathione S-transferase Mu 3 | 6, 7 | 9 |
| P21333 | Filamin A | 6 | |
| P21695 | Glycerol-3-phosphate dehydrogenase [NAD+], cytoplasmic | 11 | |
| P22061 | Protein-L-isoaspartate (D-aspartate) O-methyltransferase | 13, 14 | |
| P22314 | Ubiquitin-activating enzyme E1 | 8, 9 | |
| P23141 | Liver carboxylesterase 1 | 14, 15 | |
| P23142 | Fibulin-1 | 5 | 14, 13, 15 |
| P23528 | Cofilin, non-muscle isoform | 12, 13, 14 | 13 |
| P24534 | Elongation factor 1-beta | 3 | |
| P24592 | Insulin-like growth factor binding protein 6 | 14 | 14, 13, 15 |
| P25786 | Proteasome subunit alpha type 1 | 14 | 13 |
| P25788 | Proteasome subunit alpha type 3 | 6 | |
| P26038 | Moesin | 3, 5, 7, 12, 13, 14 | |
| P26641 | Elongation factor 1-gamma | 11 | |
| P27169 | Serum paraoxonase/arylesterase 1 | 3 | |
| P27348 | 14-3-3 protein tau | 3, 6 | |
| P28072 | Proteasome subunit beta type 6 | 4 | |
| P28161 | Glutathione S-transferase Mu 2 | 6, 11, 13, 14 | |
| P28827 | Receptor-type protein-tyrosine phosphatase mu | 5 | |
| P29218 | Inositol-1 [or 4]-monophosphate | 5, 6 | |
| P29401 | Transketolase | 7 | |
| P30040 | Endoplasmic reticulum protein ERp29 | 10 | |
| P30041 | Peroxiredoxin 6 | 5, 7, 8, 9, 10, 11, 12, 13, 14 | |
| P30044 | Peroxiredoxin 5, mitochondrial | 14 | 13 |
| P30086 | Phosphatidylethanolamine-binding protein (PEBP) | 13, 14, 15 | 7, 14, 13 |
| P30101 | Protein disulfide-isomerase A3 | 10 | |
| P30626 | Sorcin (22 kDa protein) | 6 | |
| P30740 | Leukocyte elastase inhibitor (LEI) | 8, 10, 11, 12 | |
| P31150 | Rab GDP dissociation inhibitor alpha | 5, 7 | |
| P31946 | 14-3-3 protein beta/alpha | 3, 8 | |
| P31947 | 14-3-3 protein sigma | 3 | |
| P31948 | Stress-induced-phosphoprotein 1 | 11, 12, 14, 15 | |
| P32119 | Peroxiredoxin 2 | 5, 6, 7, 8, 9, 10 | 9, 13 |
| P34932 | Heat shock 70 kDa protein 4 | 3 | |
| P35080 | Profilin-2 | 11 | |
| P35237 | Placental thrombin inhibitor | 3, 4, 5, 7 | |
| P36955 | Pigment epithelium-derived factor | 5, 6, 7, 8, 9, 10, 11, 12 | 7, 9, 13, 5, 15 |
| P36980 | Complement factor H-related protein 2 | 14 | |
| P37837 | Transaldolase | 7, 8, 9, 11, 12, 14 | |
| P40121 | Macrophage capping protein | 10, 12, 13, 14 | |
| P40925 | Malate dehydrogenase, cytoplasmic | 1, 2, 3, 7, 8, 11, 12, 13, 14, 15 | 13, 10 |
| P41222 | Prostaglandin-H2 D-isomerase | 2, 3, 4, 5, 6, 7, 8, 9, 10, 11, 12, 13, 14, 15 | 4, 7, 9, 14, 13, 15 |
| P42126 | 3,2-trans-enoyl-CoA isomerase, mitochondrial | 13 | |
| P43652 | Afamin | 5 | 15 |
| P45381 | Aspartoacylase | 14 | |
| P46940 | Ras GTPase-activating-like protein IQGAP1 | 5 | |
| P47756 | F-actin capping protein beta subunit | 6, 7 | |
| P48637 | Glutathione synthetase | 9, 10 | |
| P49419 | Aldehyde dehydrogenase family 7 member A1 | 14 | |
| P50135 | Histamine N-methyltransferase | 6 | |

TABLE 3-continued

| UniProt Accession number | Protein name | Identified in the following post-mortem fractions[a] | Previously identified in CSF in the following references |
|---|---|---|---|
| P50395 | Rab GDP dissociation inhibitor beta | 5, 10, 11, 12, 13, 14 | |
| P51693 | Amyloid-like protein 1 | 3, 5 | 4, 14, 13, 15 |
| P51884 | Lumican | 3, 5, 7 | 13, 15 |
| P52565 | Rho GDP-dissociation inhibitor 1 | 5, 9, 10, 14, 15 | |
| P52566 | Rho GDP-dissociation inhibitor 2 | 6 | |
| P52907 | F-actin capping protein alpha-1 subunit | 7, 8 | |
| P54289 | Dihydropyridine-sensitive L-type, calcium channel alpha-2/delta subunits | 5 | |
| P54652 | Heat shock-related 70 kDa protein 2 | 5 | |
| P54764 | Ephrin type-A receptor 4 | 7 | |
| P54922 | ADP-ribosylarginine hydrolase | 12 | |
| P55287 | Cadherin-11 | 3 | |
| P55854, P61956 | Ubiquitin-like protein SMT 3A or 3B | 5 | |
| P57087 | Junctional adhesion molecule 2 | 14 | |
| P60174 | Triosephosphate isomerase | 10, 11, 12, 13, 14, 15 | 13 |
| P60709 | Actin, cytoplasmic 1 | 5, 6, 7, 8 | 7, 9 |
| P60900 | Proteasome subunit alpha type 6 | 12, 14 | |
| P61088 | Ubiquitin-conjugating enzyme E2 N | 11 | |
| P61916 | Epididymal secretory protein E1 | 8 | 7, 14, 15 |
| P61981 | 14-3-3 protein gamma | 3, 8 | 13 |
| P62258 | 14-3-3 protein epsilon | 2, 3 | |
| P62937 | Peptidyl-prolyl cis-trans isomerase A | 12, 14, 15 | 13, 15 |
| P62988 | Ubiquitin | 14 | 4, 9, 13 |
| P62993 | Growth factor receptor-bound protein 2 | 11, 14 | |
| P63104 | 14-3-3 protein zeta/delta | 3, 6, 8 | |
| P63261 | Actin, cytoplasmic 2 (Gamma-actin) | 7 | 13 |
| P67936 | Tropomyosin alpha 4 chain | 3 | |
| P68133 | Actin, alpha skeletal muscle | 9 | |
| P68871 | Hemoglobin beta chain | 12, 13, 14 | 7, 9, 13, 5 |
| P78324 | Tyrosine-protein phosphatase non-receptor type substrate 1 | 12, 14 | 14, 13, 15 |
| P78417 | Glutathione transferase omega 1 | 10, 12 | 13 |
| P81605 | Dermcidin | 5 | 7, 15 |
| P98160 | Basement membrane-specific heparan sulfate proteoglycan core protein | 8, 10 | 9, 13, 15 |
| Q00169 | Phosphatidylinositol transfer protein alpha isoform | 14 | |
| Q01082 | Spectrin beta chain, brain 1 | 5 | |
| Q01469 | Fatty acid-binding protein, epidermal (E-FABP) | 12, 13 | 13 |
| Q01995 | Transgelin | 12, 14 | |
| Q03591 | Complement factor H-related protein 1 | 9, 12 | |
| Q02246 | Contactin 2 | 14 | 10, 15 |
| Q04917 | 14-3-3 protein eta | 3 | |
| Q06033 | Inter-alpha-trypsin inhibitor heavy chain H3 | 5 | |
| Q06830 | Peroxiredoxin 1 | 12, 13, 14, 15 | 13 |
| Q07898 | M130 antigen, CD163 | 4, 5 | 15 |
| Q12765 | Secernin 1 | 3 | |
| Q12860 | Contactin 1 | 5, 6, 7, 8, 9, 10 | 9, 13 |
| Q13228 | Selenium-binding protein 1 | 5, 10, 12 | 13 |
| Q13332 | Receptor-type tyrosine-protein phosphatase S | 10 | |
| Q13449 | Limbic system-associated membrane protein | 3 | 13, 15 |
| Q13509 | Tubulin beta-4 | 5 | |
| Q13740 | CD166 antigen | 5 | |
| Q13813 | Spectrin alpha chain, brain | 5 | |
| Q13938 | Calcyphosine | 3 | |
| Q14118 | Dystroglycan | 5 | 13, 15 |
| Q14126 | Desmoglein 2 | 3 | |
| Q14515 | SPARC-like protein 1 | 3, 12 | 14, 13, 15 |
| Q14624 | Inter-alpha-trypsin inhibitor heavy chain H4 | 3, 4, 5, 6, 7, 8 | 14, 13 |
| Q15149 | Plectin 1 | 8 | |
| Q15181 | Inorganic pyrophosphatase | 8 | |
| Q15818 | Neuronal pentraxin-1 | 12 | 15 |
| Q16270 | Insulin-like growth factor binding protein 7 | 11, 14, 15 | 13, 15 |
| Q16555 | Dihydropyrimidinase related protein-2 | 8, 9 | 13 |
| Q16620 | BDNF/NT-3 growth factors receptor | 3 | |
| Q16881 | Thioredoxin reductase 1, cytoplasmic | 12 | |
| Q7Z664 | Hypothetical protein DKFZp779N0926 (Fragment) | 8 | |
| Q7Z7P9 | PHYHD1 protein | 11 | |
| Q86UP2 | Kinectin | 7 | |

TABLE 3-continued

| UniProt Accession number | Protein name | Identified in the following post-mortem fractions[a] | Previously identified in CSF in the following references |
|---|---|---|---|
| Q8N0Y7 | Putative phosphoglycerate mutase 3 | 14 | |
| Q8N240 | Hypothetical protein FLJ34957 | 12 | |
| Q8NCW5 | ApoA-I binding protein precursor | 7 | |
| Q8NFZ8 | TSLC1-like 2 | 3, 5, 6, 7, 8, 9 | |
| Q8TAG5 | Immunoglobulin-like domain protein MGC33530 | 8 | |
| Q8TD26 | Chromodomain-helicase-DNA-binding protein 6 | 5, 6 | |
| Q92520 | Protein FAM3C | 7, 14 | 7, 13, 15 |
| Q92598 | Heat shock protein 105 kDa | 3 | |
| Q92823 | Neuronal cell adhesion molecule | 4, 5, 7, 8, 10, 12, 14 | 15 |
| Q92876 | Kallikrein 6 | 14, 15 | 7, 9, 13, 5, 15 |
| Q92890 | Ubiquitin fusion degradation protein 1 homolog | 5 | |
| Q96AC3 | Secernin 2 | 9 | |
| Q96EI3 | PTD012 protein | 14 | |
| Q969H8 | Protein C19 or F10 precursor | 15 | |
| Q96IU4 | CCG1-interacting factor B | 11 | |
| Q96KN2 | Glutamate carboxypeptidase-like protein 2 | 5 | 14, 13, 15 |
| Q96NV4 | Hypothetical protein FLJ30028 | 12 | |
| Q96NY7 | Chloride intracellular channel 6 | 3, 5 | 13 |
| Q99497 | DJ-1 protein | 8, 9, 11, 13 | 13, 15 |
| Q9BX68 | Histidine triad nucleotide-binding protein 2 | 14 | |
| Q9H008 | Phospholysine phosphohistidine inorganic pyrophosphate phosphatase | 15 | |
| Q9H2Y2 | Inositol 1-phosphate synthase | 7, 8, 9 | 13 |
| Q9H3J8 | My027 protein | 7, 8 | |
| Q9H477 | Ribokinase | 4 | |
| Q9NQ56 | Leucine zipper transcription factor-like 1 | 7 | |
| Q9NVS9 | Pyridoxine-5'-phosphate oxidase | 11, 12 | |
| Q9NX46 | Hypothetical protein FLJ20446 | 5 | |
| Q9P0L0 | Vesicle-associated membrane protein-associated protein A | 14 | |
| Q9P121 | Neurotrimin | 3 | |
| Q9P1W8 | Signal-regulatory protein beta-2 | 14 | |
| Q9P2S2 | Neurexin 2-alpha | 12 | 13 |
| Q9UBP4 | Dickkopf related protein-3 | 1 | 13, 15 |
| Q9UBQ7 | Glyoxylate reductase/hydroxypyruvate reductase | 14 | |
| Q9UKK9 | ADP-sugar pyrophosphatase | 3 | |
| Q9UKX2 | Myosin heavy chain, skeletal muscle, adult 2 | 9 | |
| Q9UN36 | NDRG2 protein | 5, 6 | |
| Q9Y5Z5 | Heme-binding protein | 8 | |
| Q9Y617 | Phosphoserine aminotransferase | 12, 14, 15 | |
| Q9Y623 | Myosin heavy chain, skeletal muscle, fetal | 9 | |
| Q9Y6R7 | Human Fc gamma BP (Fragment) | 14 | |

Figure 8:
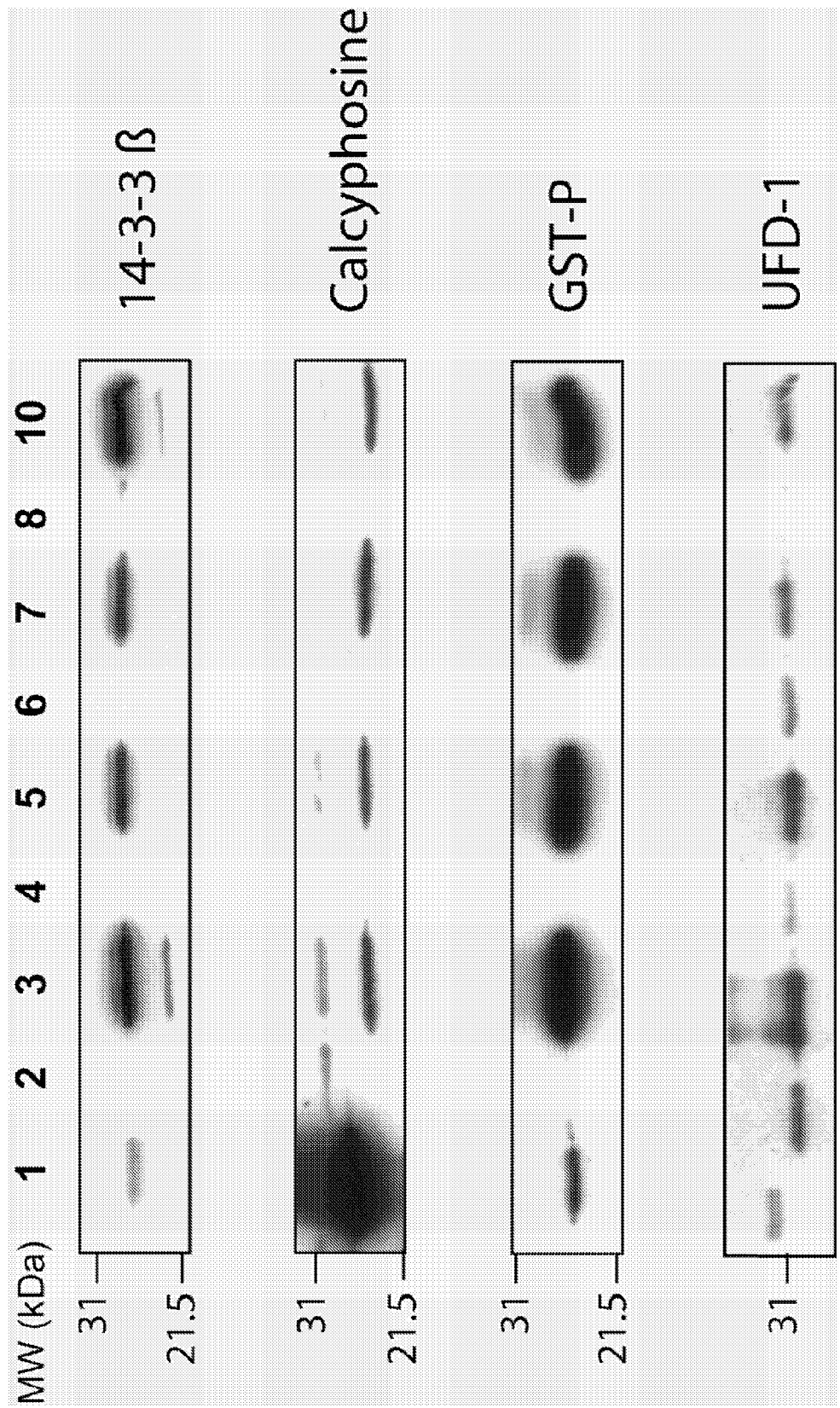
FIG. 8 shows Western blots of four proteins that were identified only in postmortem fractions of CSF.

[a] Bold numbers indicate fractions in which the protein was identified from a single peptide Identification Validation by Immunoblot:

Proteins of specific interest, such as proteins that were only identified in postmortem CSF fractions or those known to be associated with brain disorders, were further investigated using immunoblots. FIG. 8 shows Western blots of four proteins that were identified only in postmortem fractions. As described in the methods section, unfractionated CSF samples were separated on an SDS-PAGE gel and then electroblotted on to a PVDF membrane. The membrane was then probed for proteins of interest using specific antibodies. The results for the 14-3-3 protein beta, calcyphosine, GST-P, and UFD1 are shown in FIG. 8. For the first three proteins, evidence for their increased concentration in postmortem CSF compared to ante-mortem CSF is clear from the strong signal apparent in each of the postmortem CSF samples but not in the ante-mortem samples. The result is less clear for UFD1, but an increased concentration of this protein in the postmortem CSF samples is still apparent. Other isoforms of the 14-3-3 protein were also tested (epsilon, gamma, teta, zeta) and gave results identical to isoform beta (data not shown).

Localization and Functional Classification:

Bibliographic searches of the proteins identified from the Swiss-Prot database enabled their classification by their putative localization and function. Classical circulating proteins (51%) and secreted proteins (9%) together represented the majority of the proteins identified in the ante-mortem CSF fractions. In contrast, most of the proteins identified in the postmortem CSF sample had a putative intracellular localization (57.5%) and there was a lower proportion of classical circulating proteins (21%) and secreted proteins (3%). Considering proteins identified only in the postmortem CSF fractions, more than 75% were found to have a putative intracellular localization. These data strongly suggest that most of these proteins arose in postmortem CSF by tissue leakage. Differences were also noted in the functions represented by the proteins identified in ante-mortem CSF compared to postmortem CSF. In ante-mortem CSF, numerous proteins were found to be involved in protein binding and transport, coagulation, immunity or inflammation. In postmortem CSF, the proportion of these functional classes was much lower whilst the proportion of functional classes such as enzymes, structural proteins, and signal transduction proteins was higher. The majority of the proteins identified uniquely in the postmortem CSF pool were associated with intracellular functions including metabolic enzymes, structural proteins, and proteins involved in signal transduction pathways and protein metabolism.

Discussion

A previous 2-DE study identified several proteins with increased levels in postmortem CSF compared to ante-mortem CSF. Further validation studies showed the potential interest of some of these proteins as biochemical markers of various neurological disorders. The goal of the present study was to further characterize the postmortem CSF proteome in order to identify new potential markers of brain damage.

We performed a parallel analysis of pooled ante-mortem and postmortem CSF samples using a protocol combining several steps of protein fractionation prior to protein identification by MS. A total of 115 proteins was identified in the ante-mortem pool and 299 in the postmortem pool, resulting in a total of 316 distinct protein identifications. Comparison between the ante-mortem and postmortem protein lists indicated that 201 proteins were uniquely identified in the postmortem CSF fractions. In order to reduce the risk of introducing differences between the samples due to technical bias, each step of the analysis was carefully controlled. For protein depletion, we used a highly specific method based on immunoaffinity subtraction chromatography. This system minimizes the risk of non-specific protein removal. CSF proteins were further fractionated according to their pI using OGE. The OGE technique has been shown to reliably separate proteins with a resolution up to 0.15 pH units. Immunodetection of the gamma isoform of the 14-3-3 protein in only a single fraction of the postmortem fractions following OGE confirmed the resolving power of the technique. SDS-PAGE and 2-DE gel analysis of replicate fractionations of ante-mortem and postmortem CSF samples also confirmed the high reproducibility of OGE (data not shown). In the current study, OGE fractionation of ante-mortem and postmortem samples was performed in the same run using a multiwell device in order to avoid inter-assay variations. The fractions obtained from OGE were separated by SDS-PAGE. Corresponding ante- and postmortem protein fractions were always loaded on the same gel. After silver staining, the gel lanes were sliced using an identical pattern for corresponding ante- and postmortem fractions. In-gel protein digestion and peptide extraction were performed in parallel for corresponding ante- and postmortem fractions. In the final step of the protocol, proteins were identified by LC-ESI-MS/MS analysis using an ion-trap mass spectrometer. Data-dependant LC-ESI-MS/MS analysis is often considered to be poorly reproducible between replicate data acquisitions. This is generally the case for large-scale proteome studies investigating very complex protein samples. In the study presented here, LC-ESI-MS/MS analysis was performed on peptides extracted from small SDS-PAGE gel bands. This approach reduced the complexity of the peptide mixture analyzed and lowered the risk of missed protein identifications. Immunoblot experiments were performed in order to check that differences between the ante- and postmortem protein lists really corresponded to differences in protein concentration. Results obtained from both unfractionated CSF samples and OGE fractions confirmed results of the LC-ESI-MS/MS analysis.

The use of postmortem CSF as a source of potential protein markers of brain damage was based on the assumption that the global brain necrosis following death results in protein leakage from damaged tissues into CSF, thereby mimicking events associated with brain tissue lesions in various neurological disorders. Accordingly, 75% of the 201 proteins identified uniquely in the postmortem CSF sample had a putative intracellular location, most likely due to their leakage from damaged brain cells. In addition, most of the proteins identified from postmortem CSF were found to be associated with intracellular functions (metabolic enzymes, structural proteins, signal transduction proteins and proteins involved in synthesis and degradation). Further support for the argument that most of the proteins specifically identified in postmortem CSF arose from tissue leakage came from the comparison of our results with previous studies of CSF from healthy subjects. Approximately 70% of the proteins identified in the ante-mortem CSF pool have already been described in at least one of these studies. In contrast, only 15% of the proteins detected uniquely in the postmortem CSF pool were reported in these previous studies. Since the ante- and postmortem samples were analyzed under identical conditions, this discrepancy suggests that most of the proteins identified uniquely in the postmortem sample are either absent in healthy ante-mortem CSF or present at very low levels. Their detection was presumably facilitated in postmortem CSF following their release from damaged cells.

Bibliographic searches of the 201 proteins specifically identified in postmortem CSF also revealed that a number of them had previously been described as potential markers of brain disorders. For example, H-FABP and DJ-1, which were previously identified in the postmortem CSF 2-DE study, have been validated as potential early plasmatic markers of stroke. H-FABP was also shown to be a potential marker of CJD and other neurodegenerative dementias. Glial fibrillary acidic protein and creatine kinase BB have been described as potential markers of various brain damage-related disorders, although their clinical utility has been questioned. We also identified several isoforms of the 14-3-3 protein, which is a known CSF marker of CJD. Another interesting finding was the identification in postmortem CSF of a fragment of the brain spectrin alpha-chain. Spectrin fragments, called spectrin breakdown products (SBPs), are produced in a variety of neurodegenerative conditions by caspase-3 and calpain-mediated proteolysis. They are particularly stable and were proposed as potential CSF markers of traumatic brain injury. The fragment identified in this study had a molecular weight of approximately 120 kDa, corresponding to a specific SBP produced by caspase-3 proteolysis.

Many additional protein identifications from this study are of interest as potential markers of brain disorders owing to their elevated levels in postmortem CSF compared to ante-mortem CSF. From the list of 201 proteins uniquely identified in postmortem CSF, several have been highlighted since they have been reported to be brain specific, have high expression levels in the brain and/or have been associated with nervous system injury or pathology. A total of 22 proteins have been selected using these criteria (Table 4).

TABLE 4

| | | | Brain specific | Highly expressed in brain | Potential link with neurological disorders | Other |
|---|---|---|---|---|---|---|
| Glutathione S-transferase Mu 2 | 25 | 613/6.02 | | * | | 1 |
| Glutathione S-transferase Mu 3 | 26 | 428/5.37 | | * | | 1 |
| Aflatoxin B1 aldehyde reductase member 2 | 39 | 589/6.70 | | * | * | |
| Aspartoacylase | 35 | 735/6.06 | | * | * | |
| Fructose-bisphosphate aldolase C | 39 | 325/6.46 | * | | * | |
| NG,NG-dimethylarginine dimethylaminohydrolase 1 | 30 | 991/5.53 | | * | * | 2 |
| Phosphoserine aminotransferase | 40 | 423/7.56 | | * | | |
| Pyruvate kinase, isozymes M1/M2 | 57 | 931/7.59 | | * | * | |
| Cadherin-11 | 81 | 986/4.50 | | * | | 3 |
| CD166 antigen | 62 | 293/5.71 | | * | | 3 |
| Contactin 2 | 107 | 467/7.26 | * | | | 3 |
| Neurotrimin | 31 | 738/5.80 | * | | | 3 |
| SPARC-like protein 1 | 73 | 577/4.66 | | * | | 3 |
| BDNF/NT-3 growth factors receptor | 88 | 319/5.86 | | * | * | 4 |
| Dihydropyridine-sensitive L-type, calcium channel alpha-2/delta subunits | 104 −16 | 304/5.30 466/4.47 | | * | | 5 |
| Inositol-1 [or 4]-monophosphate | 30 | 189/5.16 | | * | * | |
| Receptor-type protein-tyrosine phosphatase mu | 161 | 704/6.13 | | * | | 3 |
| Receptor-type tyrosine-protein phosphatase F | 210 | 283/5.94 | | * | | 6 |
| Spectrin alpha chain, brain | 284 | 527/5.22 | | * | * | |
| Spectrin beta chain, brain 1 | 274 | 631/5.41 | | * | * | |
| Alcohol dehydrogenase [NADP+] | 36 | 442/6.35 | | * | | |
| Chromodomain-helicase-DNA-binding protein 6 | 305 | 153/5.89 | | ? | | |
| Dihydropyrimidinase related protein-2 | 62 | 294/5.95 | | * | * | 7 |
| Histidine triad nucleotide-binding protein 2 | 17 | 162/9.20 | | ? | | |
| Immunoglobulin-like domain protein MGC33530 | 24 | 453/7.77 | | ? | | |
| NDRG2 protein | 40 | 798/5.08 | | * | * | |
| Neurexin 2-alpha | 182 | 042/5.55 | * | | | 8 |
| Neuronal pentraxin-1 | 45 | 393/5.84 | * | | | 8 |

1 Antioxidant protein
2 Endothelial dysfunction
3 Axonal growth
4 Neural development and survival
5 Synaptic function
6 Neural development
7 Neuronal polarity
8 Synaptogenesis These proteins all have a putative intracellular or membrane location and, with the exception of two proteins, were identified from SDS-PAGE gel bands with Mr corresponding to the theoretical MW of the full-length protein. Receptor-type protein-phosphate F and Mu were detected in gel bands with Mr of approximately 120 kDa whereas the theoretical MWs of the full-length proteins are 210 282 kDa and 161 704 kDa, respectively. Several of the proteins shown in Table 4 have also been detected in previous studies of ante-mortem CSF (see Table 2). This is unsurprising since tissue leakage products are also released at low levels from healthy tissues into body fluids (1). As methods for the identification of proteins from complex mixtures continue to attain lower limits of detection, it is anticipated that additional tissue leakage products will be found in ante-mortem CSF. In the current study, however, these proteins were identified uniquely in the postmortem fractions suggesting that their concentration in CSF was increased in the model of massive brain injury.

Taken together these data strongly suggest that the 22 selected proteins represent highly interesting potential markers of brain damage. According to our model, they were released from damaged cells into CSF following brain tissue necrosis. In addition, they have been reported to be brain specific or have high expression levels in the brain, thereby increasing the chance of being specific markers of brain injury. Furthermore, altered expression levels of several of these proteins have been found in neurological disorders or following nervous system injury. Validation studies using both serum and CSF samples from patients will determine the utility of these proteins as markers of brain damage.

Example 5

ELISA validation was performed to evaluate blood concentration of glutathione S transferase P (GSTP-1) on two independent cohorts of patients encompassing stroke with different sub-types (ischemia, hemorrhage and transient ischemic attack (TIA)) and control patients. Details of the cohorts are as follows:

Swiss Population

Plasma samples corresponded to ten controls and ten stroke patients age (birth from 1911 to 1935) and gender (7 women and 3 men) matched collected and tested in Geneva. Stroke and control patients were admitted in the Geneva university Hospital emergency unit and enrolled in this study from August 1996 to January 1997. For each patient, a blood sample was collected in dry-heparin containing tube at the time of admission. After centrifugation at 1500 g for 15 min at 4° C., plasma samples were aliquoted and stored at −20° C. until analysis. The control group (7 women and 3 men; mean age: 78.3 years; range: 66-89 years) is composed of patients suffering from various medical or surgical conditions, including cancer, gastrointestinal disorders, orthopedic and opthalmologic pathologies. None of them has a past or recent history of cerebrovascular event.

The stroke group is composed of patients diagnosed with stroke (7 women and 3 men; mean age: 74.1 years; range: 62-85 years) including 9 ischemic and 1 hemorrhagic strokes. The time interval between the neurological event and the first blood draw was ranging from inferior to 12 hours (n=6) and up to 2 days (n=2 for 24 hours and n=2 for 2 days). The diagnosis of stroke was established by a trained neurologist and was based on a sudden appearance of a focal neurologic deficit and the subsequent delineation of a lesion consistent with the symptom on brain CT or MRI images. The stroke group was separated according to the type of stroke (ischemia or hemorrhage), location of the lesion (brainstem or hemisphere) and clinical evolution over time (TIA when complete recovery occurred within 24 hours or established stroke when the neurological event was still present after 24 hours).

Spanish Cohort

Twenty-nine control and 39 stroke patients were enrolled in this study (Table 5). Tests were performed on sera samples. The stroke subgroup included 10 hemorrhagic and 29 ischemic patients. The ischemic population was divided into (i) cardioembolic among them partial (n=5) and total (n=4) anterior circulation infarct, (ii) atherothrombotic among them partial (n=5) and total (n=5) anterior circulation infarct and (iii) lacunar infarct (n=5) and TIA (n=5). The 39 stroke patients were recruited within 24 hours after onset of symptoms, and exact time was obtained for 18 patients. The average time interval between the neurological event and the first blood draw for these patients was 10.0 hours (range 30 min to 6.25 days).

TABLE 5

| Spanish cohort | Stroke | Control |
|---|---|---|
| n | 39 | 29 |
| Age mean ± SD (min-max) | 70.2 ± 12.1 (44-95) | 69.3 ± 9.5 (54-87) |
| Female n (%)/Male n (%) | 17 (43.6)/22 (56.4) | 14 (48.3)/15 (51.7) |
| Time onset of symptoms (hrs) | | — |
| mean ± SD (min-max) | 10.03 ± 29.96 (0.5-150) | |
| median (25-75 percentiles) | 3.05 (1.92-7.27) | |
| Hemorrhagic n (%) | 10 (25.6) | — |
| Ischemic n (%) | 29 (74.4) | — |
| Cardioembolic PACI n (%) | 5 (12.8) | — |
| Cardioembolic TACI n (%) | 4 (10.4) | |
| Lacunar n (%) | 5 (12.8) | |
| Atherothrombotic PACI n (%) | 5 (12.8) | — |
| Atherothrombotic TACI n (%) | 5 (12.8) | — |
| TIA n (%) | 5 (12.8) | — |

The results are shown in FIG. 9. The level of GSTP-1 was significantly higher in the blood of stroke patients in the Swiss and Spanish cohorts (p<0.0001, Mann-Whitney tests) with 100% of sensitivity and specificity in the Swiss cohort and with 72% sensitivity and 93% specificity in the Spanish cohort.

This result demonstrates that GSTP-1 is a useful marker for early diagnosis of stroke, alone, or in combination with other biomarkers.

As GSTP-1 has been found over-expressed in deceased CSF, it is a reasonable prediction that other polypeptides and proteins differentially expressed in deceased CSF will also be useful as markers for brain damage-related disorders.

Example 6

Validation of APO-AIV Fragments as Diagnostic Markers of Alzheimer's Disease Using Western Blotting Apolipoprotein A-IV (ApoA-IV) was first identified in the proteomic analysis of CSF described in Example 4 above. To evaluate its utility in diagnosis of brain damage-related disorders its presence in the plasma of patients with Alzheimer's disease (AD) was studied using Western blotting.

Plasma samples were diluted 1:10 with double distilled water and assayed using a Bradford dye-binding method (diluted samples permit handling of suitably sized aliquot volumes).

SDS-PAGE was carried out using 20 µg sample per lane (2 µg if sample is a denatured primary or secondary antibody) on 16% acrylamide gels, 1.5 mm thick, 10 wells (NOVEX) for 1 hr 80 V; 11 hrs 125 V. This was followed by Western Blotting onto nitrocellulose membrane at 50 V for 1½ hrs. The blots were probed with the following antibodies:

Anti-ApoA-IV (N-terminal specific), Santa Cruz Biotechnology, Inc.

Anti-ApoA-IV (C-terminal specific), Santa Cruz Biotechnology, Inc.

Figure 10:
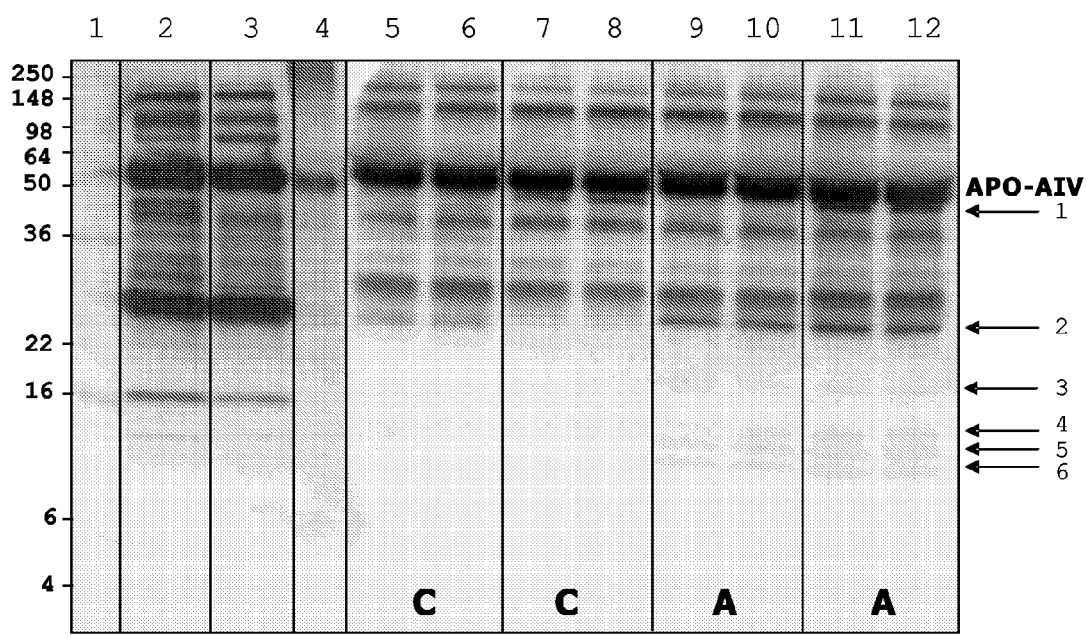
FIG. 10 shows Western blot validation of Apolipoprotein A-IV in Alzheimer's disease, as described in Example 6.

Both antibodies are affinity purified goat polyclonals raised against a peptide mapping near the amino (N-terminal) or carboxy (C-terminal) terminus of ApoA-IV of human origin. These antibodies were chosen since probing for the N- and C-terminals should increase the chance of detection of the ApoA-IV protein and/or fragments. The results of this analysis are shown in FIG. 10.

Several bands were found that appear to be ApoA-IV specific and also discriminatory for AD. These bands do not appear in the secondary antibody-only control blot for control or AD samples.

Bands 3-6 which are observed in the 10-16 kDa region are discriminatory for AD, but also appear to align with bands in the denatured ApoA-IV antibody lanes. It has also been observed that bands 3-6 are much stronger on blots where the N-terminal specific anti-ApoA-IV antibody has been used.

Two other key bands are observed. Band 1 is observed at approximately 45 kDa and appears to correspond to the full length mature APO-AIV protein. Band 2 is observed at approximately 28 kDa and appears to be an N-terminal fragment of APO-AIV.

Example 7

Validation of Complement Factor H as Diagnostic Markers of Alzheimer's Disease using Western Blotting Complement Factor H(CFH) was first identified in the proteomic analysis of CSF described in Example 4 above. To evaluate its utility in diagnosis of brain damage-related disorders its presence in the plasma of patients with Alzheimer's disease (AD) was studied using Western blotting.

Plasma samples were diluted to 1 in 8 in Phosphate buffered saline (PBS). An equal volume of Laemmli 2× sample buffer was added and boiled for 10 min until use.

Western Blot

SDS gel electrophoresis was performed using the Fisher Scientific 36 well, 1.5 mm gels (all solutions were purchased from National Diagnostics). Samples were separated on a 10% resolving gel with a 4% stacking gel (all solutions were purchased from National Diagnostics). Samples (20 µl) were separated initially for 30 min at 110V and then for 60 min at 150V until the dye front just began to enter the running buffer.

The gel was transferred to PVDF (Amersham Biosciences) using a Semi-dry transblot (Bio-Rad) for 45 min at 15V. The membrane was then blocked in 5% milk made in PBS-Tween and probed with Complement factor H primary antibody (Abcam, UK) overnight at 4° C. The bands were detected with a chemiluminescence Western detection kit (ECL+, Amersham Biosciences) and the membranes were scanned using Storm fluorescence scanner (Amersham Biosciences).

An immunoreactive band was observed at 139 kDa (CfH) and the optical density was quantified using the Image Quant (Amersham Biosciences) software. Analysis was by non-parametric Mann-Whitney using the SPSS package.

Results

Western blot data was acquired from plasma from 128 people with NINCDS-ADRDA probable AD and 78 normal healthy elderly controls. Cases with AD had a 32% increase in CFH (Mann-Whitney; Table 6).

TABLE 6

| Diagnosis | Number | Mean CFH | SD | SEM |
| --- | --- | --- | --- | --- |
| Controls | 128 | 65.6 | 65.5 | 5.8 |
| Probable AD | 78 | 96.0 | 96.8 | 11.0 |

There was a gender difference with a relatively higher CFH value in females overall relatives to males (p=0.05). However CFH was higher in cases with AD relative to controls even when considering genders separately (p<0.01; Table 7).

TABLE 7

| Females only | Number | Mean CFH | SEM |
| --- | --- | --- | --- |
| Controls | 78 | 73.0 | 8.9 |
| Probable AD | 64 | 102.7 | 13.0 |
| Total | 142 | 86.4 | 7.7 |

A receiver operator curve (ROC) analysis showed that CFH performs better than chance as a diagnostic test.

To further evaluate the performance of CFH as a diagnostic plasma marker for AD levels of CFH were determine using the same Western blot methodology in a number of clinically similar dementias. It was shown that CFH levels were only significantly elevated relative to controls in the AD cohort and not in any other dementias.

Example 8

Validation of Complement Factor 3a as Diagnostic Marker of Alzheimer's Disease

1. Summary:

In this study, it was possible to show for plasma samples that the concentration of the C3a peptide of individuals with Alzheimer's disease (AD) is changed.

2. Introduction:

C3 is a glycoprotein of 180 kDa that acts as a component of the complement system. It activates the complement system, being processed by the removal of four arginin residues to form two chains, α and β, linked by a disulphide bond. In a proteolytic event the 77 amino acid residue long C3a peptide (anaphylatoxin) of 4 kDa is subsequently released from the α chain. C3a has been shown to be a pro-inflammatory and an anti-inflammatory mediator that binds to C3aR, a G-protein coupled receptor.

The aim of this study was the quantitative determination of the C3a peptide in human plasma samples from a control and a case (AD) group.

3. Experimental Procedure:

In these experiments, we analysed human plasma samples using a commercial C3a ELISA assay (BD OptEIA Cat. No. 550499) from BD Biosciences (San Diego, Calif. 92121 (USA)). The plates were washed in the instrument Powerwasher384 from Tecan GmbH (Crailsheim, Germany) and, subsequently, measured in a GeniosPro absorbance reader from Tecan GmbH (Crailsheim, Germany) at 450/620 nm with 10 reads per well. All procedures were carried out according to the manufactures' instructions. The human plasma samples were diluted 1:500 prior to analysis.

In this method, C3a standards or patient samples from either a case (AD) or a control group are first added to wells that were coated before with C3a-desArg monoclonal antibodies. After washing of the wells a mixture of biotinylated polyclonal anti-human C3a antibody and streptavidin-horseradish peroxidase is added, producing an antibody-antigen-antibody sandwich. The activity of the enzyme present on the surface of the well is being quantitated by reaction with a suitable substrate (TMB) to produce colour. As controls the assay includes C3a standard solutions with a concentration range from 0 to 5 ng/ml.

Two experiments were performed: experiment 1 with 20 patient samples per group and experiment 2 with 30 patient samples per group (the experiment 2 was a repeat of experiment 1 with another 10 patient samples per group). Each patient and control sample was analysed in double.

In order for the assay results to be considered valid the concentrations of the controls must meet certain criteria as given by the manufacturer. For the standard curves of experiment 1 and 2 coefficients of determination of 0.995 and 0.998 have been determined, respectively. Furthermore, the measured absorbance values were statistically analysed by a two-tailed t-test (statistiXL program package 1.5).

Figure 11:
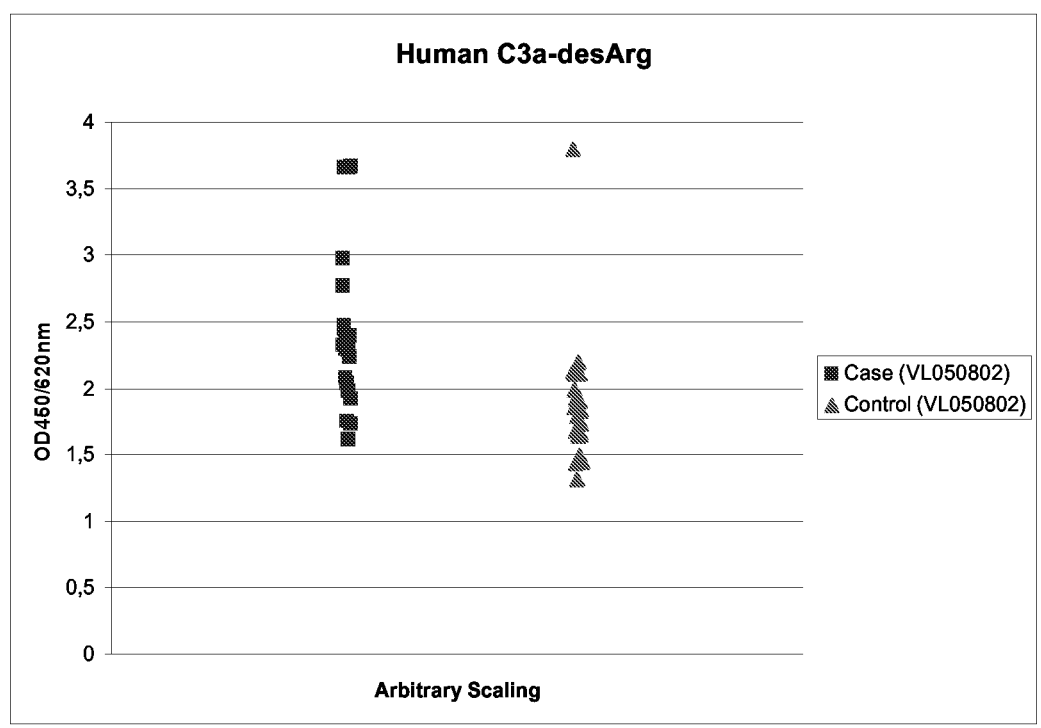
FIG. 11 is a scatter plot of values for Complement Factor 3a in plasma from Alzheimer's disease patients and controls, as described in Example 8.

4. Results and Discussion:

Among the individual absorbance values a significant biological variation was observed for both the control and the case group (coefficient of variation in experiment VL050802: 26 and 27%; coefficient of variation in experiment VL051012: 37 and 30%). The scatter plot in FIG. 11 show the measured values for the first ELISA experiments. In both experiments the difference between the two groups was found to be statistically significant as was indicated by the probability values of 0.005 and 0.003. The calculated ratios (Control/AD) for the abundance of C3a were 0.77 and 0.76 in the two ELISA experiments (see Table 8). These ratios indicate a weak modulation of the C3a expression in plasma samples of AD patients.

TABLE 8

C3a modulations from the ELISA experiments

| Data source | Case group, Medium Abs. 450 nm | Control group, Medium Abs. 450 nm | Control/Case |
|---|---|---|---|
| 1st ELISA Experiment (VL050802) | 2.428 ± 0.626 | 1.881 ± 0.515 | 0.77 |
| 2nd ELISA Experiment (VL051012) | 2.310 ± 0.687 | 1.769 ± 0.654 | 0.76 |

This result demonstrates that Complement Factor 3a is a useful marker for Alzheimer's disease, alone, or in combination with other biomarkers.

As Complement Factor 3a has been found over-expressed in deceased CSF, it is a reasonable prediction that other polypeptides and proteins differentially expressed in deceased CSF will also be useful as markers for brain damage-related disorders.

Example 9

A list of proteins observed in post-mortem CSF was supplied based on Examples 1 and 4 above. The list was examined to find those proteins, which had been previously noted to change in expression in other experimental paradigms such as transgenic mice studied in the context of Alzheimer's Disease (PRO-TAMAD project).

Results

Table 9 indicates the subset of proteins observed in human post-mortem CSF which also show differential expression in the hippocampus material isolated from transgenic mice studied within the PRO-TAMAD project. In this respect, reference is made to WO 2006/021810.

TABLE 9

The overlap of Candidate Tissue Biomarkers of AD (mice) with proteins observed in the analysis of human postmortem CSF

| Protein Name | Mouse | Human | Function | Behaviour in PRO-TAMAD study |
|---|---|---|---|---|
| Apolipoprotein E | P08226 | P02649 | Risk factor for AD and is implicated in other neurological conditions. Involved in the processing of lipoprotein particles and is secreted in plasma. | Up-regulated in all transgenic conditions (ROH) |
| Glutathione S-transferase Mu 1*** | P10649 | P09488 | Conjugation of reduced glutathione to many substrates | 2DE spot absent from all transgenic conditions |
| Tubulin beta-4 chain*** | Q9D6F9 | Q13509 | Tubulin is the major constituent of microtubules. It binds two moles of GTP | 2DE spot absent in double transgenic |
| Ubiquitin carboxyl-terminal hydrolase isozyme L1 | Q9R0P9 | P09936 | Ubiquitin-protein hydrolase involved in the processing of ubiquitin precursors and of ubiquinated proteins. | Down-regulated in both single transgenic conditions |
| Transgelin 3 Neuronal protein Np25*** | Q9R1Q8 | Q01995 | Actin binding | Down-regulated in transgenic conditions |
| Rab GDP dissociation inhibitor 1*** | P50396 | P31150 | Regulates the GDP/GTP exchange reaction. Highly expressed in the brain | Up-regulated in transgenic conditions |

TABLE 9-continued

The overlap of Candidate Tissue Biomarkers of AD (mice) with
proteins observed in the analysis of human postmortem CSF

| Protein Name | Mouse | Human | Function | Behaviour in PRO-TAMAD study |
|---|---|---|---|---|
| Dihydropyrimidinase-like 2 (DRP-2) | P47942 | Q16555 | Involved in the formation of neurons | Observed to change in numerous studies and is generally considered to be a post-mortem artefact |
| Aspartate aminotransferase cytoplasmic | P05201 | P17174 | Catalytic activity: L-aspartate + 2-oxoglutarate = oxaloacetate + L-glutamate | Several 2DE spots down-regulated in multiple transgenic conditions |
| Fructose-bisphosphate aldolase C | P05063 | P09972 | Brain-type aldolase Glycolysis; sixth step | Down-regulated in the single transgenic conditions |
| Proteasome subunit alpha type 6*** | Q9QUM9 | P60900 | Protease involved in non-lysosomal proteolytic pathway | Exhibits a 2 fold decrease in the hippocampus of double transgenic mice |

Notes:
***Denotes those proteins which have not been previously cited to be present in human CSF
ROH = Rest of Hemisphere Conclusions The knowledge of proteins circulating in CSF as a consequence of brain damage, in this instance post-mortem, is an extremely useful resource. The task of linking various subsets of these proteins to other neurological conditions can be easily undertaken and this Example demonstrates how a simple review of legacy data can provide further evidence to support key candidate proteins as biomarkers of a particular disease.

In considering the historical PRO-TAMAD data, there appears to be considerable overlap with the proteins observed to change in the hippocampus and rest of hemisphere (ROH) tissue of the transgenic mice model of Alzheimer's disease. Ten of the original seventeen proteins reported in the PRO-TAMAD study have now been shown to be present in post-mortem human CSF and notably five of these have never been previously cited in CSF. Taken together these findings suggest further importance of these proteins in neurological diseases, Alzheimer's disease particularly. Not only have we shown changes that correlate with disease response within brain tissue, albeit in the mouse, but we have now also observed the appearance of these proteins in the CSF as a consequence of tissue damage.

Comparison of protein changes across different experimental paradigms is therefore useful and represents a valuable exercise which can be used to establish the utility of particular protein entities as biomarkers that bridge between species, tissues and body fluids. Consequently such an exercise should be a routine consideration when biomarker discovery experiments produce new candidates.

Example 10

A case-control study was performed using two dimensional gel electrophoresis analysis of plasma followed by mass spectrometry to identify the proteins differing between an Alzheimer's disease group and a control group. These were then validated by western blotting. For proteomics analysis 50 people with AD were recruited through secondary services and 50 normal elderly controls through primary care. For validation purposes a total of 511 subjects with AD and other neurodegenerative disease and normal elderly controls were examined.

Image analysis of the protein distribution of the gels alone identifies cases with AD with 56% sensitivity and 80% specificity. Mass spectrometric analysis of the changes observed in two dimensional electrophoresis identified a number of proteins previously implicated in AD pathology, including complement factor H (CFH) precursor and α-2-Macroglobulin ($\alpha$-$_2$M). The elevation of CFH and $\alpha$-$_2$M was validated by Western blotting and CFH was shown to be specific for AD and to correlate with disease severity.

Figure 12:
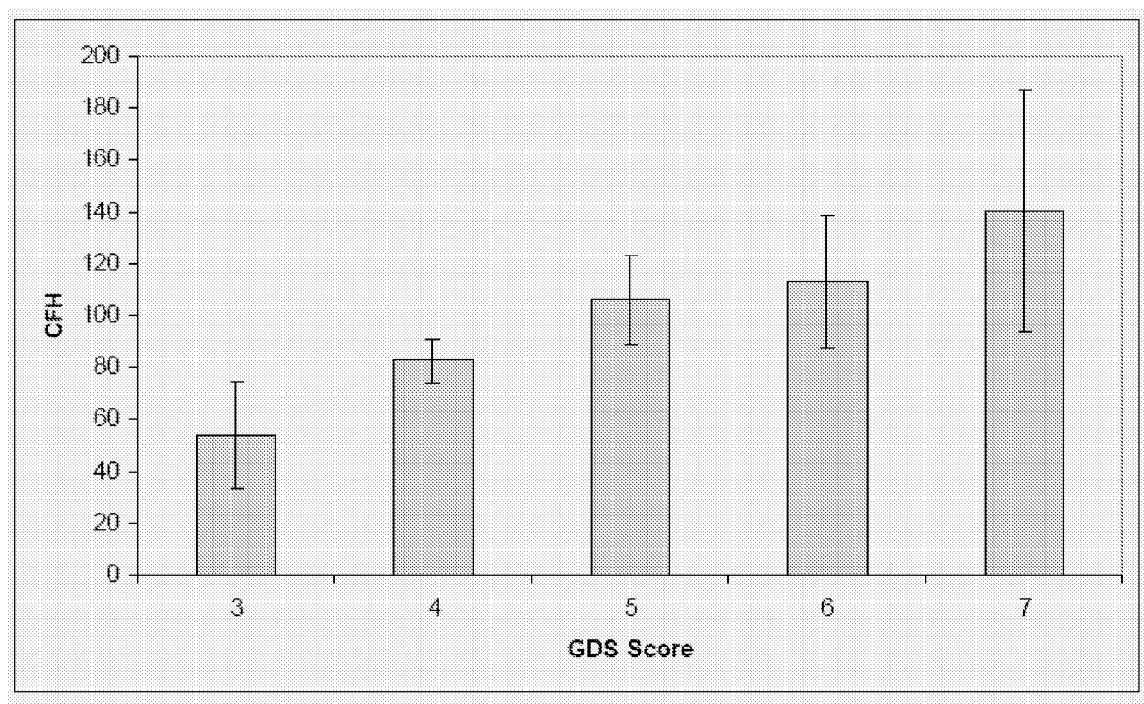
FIG. 12 shows a correlation of complement factor H levels determined by western blot with Global Dementia Scale in patients with presumed Alzheimer's disease.
Figure 13:
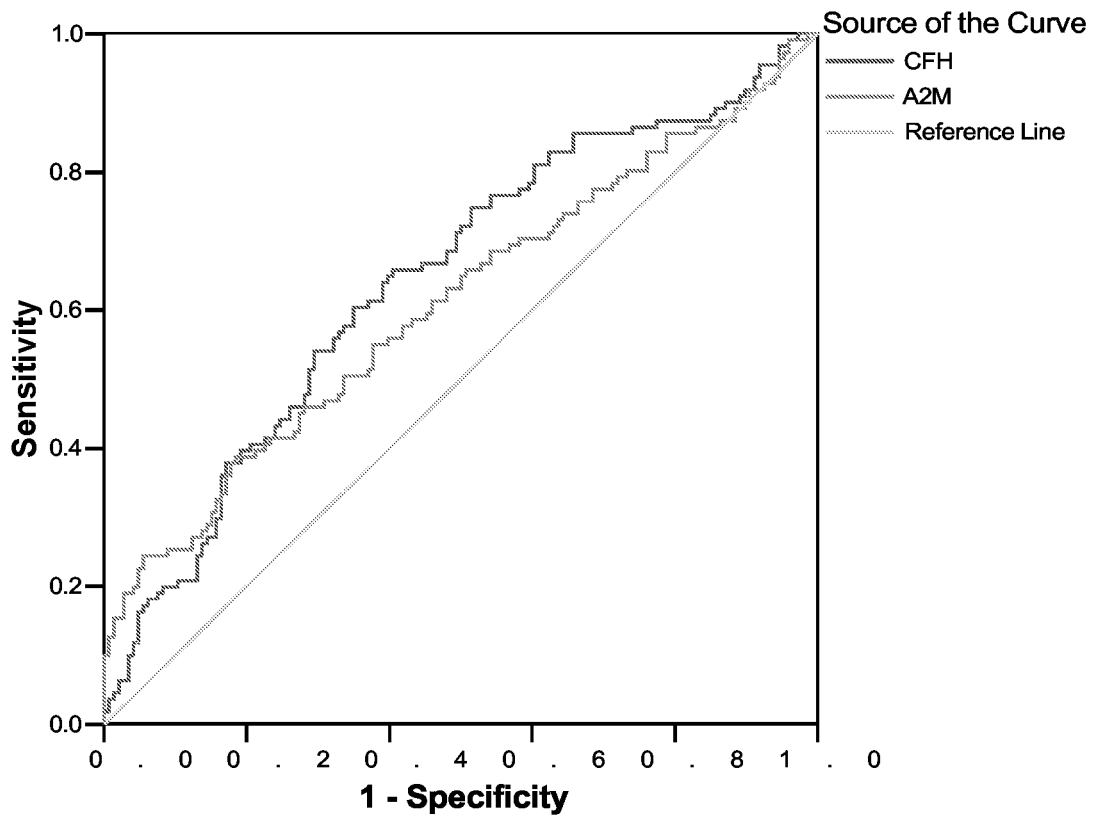
FIG. 13 is a Receiver Operating Curve (ROC) for complement factor H and alpha-2-macroglobulin as candidate plasma biomarkers of Alzheimer's disease.

Results are shown in FIGS. 12 and 13. FIG. 12 shows a correlation of complement factor H levels determined by western blot with Global Dementia Scale in patients with presumed Alzheimer's disease. FIG. 13 is a Receiver Operating Curve (ROC) for complement factor H and alpha-2-macroglobulin as candidate plasma biomarkers of Alzheimer's disease.

REFERENCES

[1] Vaagenes P, Urdal P, Melvoll R, Valnes K: Enzyme level changes in the cerebrospinal fluid of patients with acute stroke. Arch Neurol 1986; 43:357-362.

[2] Lampl Y, Paniri Y, Eshel Y, Sarova-Pinhas I: Cerebrospinal fluid lactate dehydrogenase levels in early stroke and transient ischemic attacks. Stroke 1990; 21:854-857.

[3] Matias-Guiu J, Martinez-Vazquez J, Ruibal A, Colomer R, Boada M, Codina A: Myelin basic protein and creatine kinase BB isoenzyme as CSF markers of intracranial tumors and stroke. Acta Neurol Sicand 1986; 73:461-465.

[4] Persson L, Hardemark H G, Gustafsson J, Rundstrom G, Mendel-Hartvig I, Esscher T, Pahlman S: S-100 protein and neuron-specific enolase in cerebrospinal fluid and serum: markers of cell damage in human central nervous system. Stroke 1987; 18:911-918.

[5] Cunningham R T, Young I S, Winder J, O'Kane M J, McKinstry S, Johnston C F, Dolan O M, Hawkins S A, Buchanan K D: Serum neurone specific enolase (NSE) levels as an indicator of neuronal damage in patients with cerebral infarction. Eur Clin Invest 1991; 21:497-500.

[6] Herrmann M, Vos P, Wunderlich M T, de Bruijn C H, Lamers K J: Release of glial tissue-specific proteins after acute stroke: A comparative analysis of serum concentrations of protein S-100B and glial fibrillary acidic protein. Stroke 2000; 31:2670-2677.
[7] Bitsch A, Horn C, Kemmling Y, Seipelt M, Hellenbrand U, Stiefel M, Ciesielczyk B, Cepek L, Bahn E, Ratzka P, Prange H, Otto M: Serum tau protein level as a marker of axonal damage in acute ischemic stroke. Eur Neurol 2002; 47:45-51.
[8] Watson M A Scott M G: Clinical utility of biochemical analysis of cerebrospinal fluid. Clin Chem 1995; 41:343-360.
[9] Hochstrasser D F, Frutiger S, Paquet N, Bairoch A, Ravier F, Pasquali C, Sanchez J C, Tissot J D, Bjellqvist B, Vargas R, et al.: Human liver protein map: a reference database established by microsequencing and gel comparison. Electrophoresis 1992; 13:992-1001.
[10] Sanchez J-C, Chiappe D, Converset V, Hoogland C, Binz P-A, Paesano S, Appel R D, Wang S, Sennitt M, Nolan A, Cawthorne M A, Hochstrasser D F: The mouse SWISS-2D PAGE database: a tool for proteomics study of diabetes and obesity. Proteomics 2001; 1:136-163.
[11] Hochstrasser D F Merril C R: 'Catalysts' for polyacrylamide gel polymerization and detection of proteins by silver staining. Appl Theor Electrophor 1988; 1:35-40.
[1,2] Appel R D, Palagi P M, Walther D, Vargas J R, Sanchez J C, Ravier F, Pasquali C, Hochstrasser D F: Melanie II—a third-generation software package for analysis of two-dimensional electrophoresis images: I. Features and user interface. Electrophoresis 1997; 18:2724-2734.

The invention claimed is:

1. A method of diagnosis of a brain damage-related disorder selected from stroke and sub-arachnoid hemorrhage in a subject comprising:
    (a) detecting a level of expression of glutathione S transferase P and at least one polypeptide selected from the group consisting of peroxiredoxin 1, peroxiredoxin 2, peroxiredoxin 5, and peroxiredoxin 6, or variants or mutants thereof in a sample of plasma, serum or cerebrospinal fluid taken from the subject, wherein the variants or mutants have a homology of at least 90% with the polypeptide;
    (b) detecting a level of expression of the glutathione S transferase P and the polypeptide in a control sample of plasma, serum or cerebrospinal fluid taken from a control subject known not to have suffered from the brain damage-related disorder; and
    (c) diagnosing the subject as having suffered from the brain damage-related disorder when the level-of expression of glutathione S transferase P and the at least one polypeptide in the sample is higher than the level of expression in the control sample,
    and wherein detecting the level of expression in the sample (a) and the control sample (b) comprises: immunodepletion of abundant proteins in the sample or the control sample; and assaying the immunodepleted sample or control sample using an antihuman GST-P antibody and an antibody that recognizes, binds to or has affinity for a polypeptide selected from the group consisting of peroxiredoxin 1, peroxiredoxin 2, peroxiredoxin 5 and peroxiredoxin 6 and mutants or variants thereof in the sample or the control sample, wherein the variants or mutants have a homology of at least 90% with the polypeptide.

2. The method according to claim 1, wherein the subject is diagnosed as having suffered from the brain damage-related disorder when glutathione S transferase P and the at least one polypeptide is detected in the sample, and glutathione S transferase P and the at least one polypeptide is not detected in the control sample.

3. The method according to claim 1, wherein the level of expression of glutathione S transferase P and the at least one polypeptide in the sample is at least 1.2 fold higher than the level of expression in the control sample.

4. A method of diagnosing a brain damage-related disorder selected from stroke and sub-arachnoid hemorrhage in a subject, comprising:
    contacting a plasma, serum or cerebrospinal fluid sample taken from the subject with an anti-human GST-P antibody and an antibody that recognizes, binds to or has affinity for a peroxiredoxin protein selected from the group consisting of an anti-human peroxiredoxin 1 antibody, an anti-human peroxiredoxin 2 antibody, an anti-human peroxiredoxin 5 antibody, and an anti-human peroxiredoxin 6 antibody, wherein each antibody comprises a full antibody or a functional fragment of the antibody selected from the group consisting of Fab, FAB2 and SCFv, and wherein each antibody is a biotin-conjugated antibody or an enzyme-labelled antibody;
    detecting glutathione S transferase P and a polypeptide selected from the group consisting of peroxiredoxin 1, peroxiredoxin 2, peroxiredoxin 5 and peroxiredoxin 6 and variants or mutants thereof in the plasma, serum or cerebrospinal fluid sample taken from the subject, wherein the variants or mutants have a homology of at least 90% with the polypeptide;
    contacting a control sample of plasma, serum or cerebrospinal fluid with the antibody; and
    diagnosing the subject as having the brain damage-related disorder based on an increased binding of the antibody to the polypeptide in the sample from the subject as compared with binding of the antibody in the control sample.

5. A method of diagnosing a brain damage-related disorder selected from stroke and sub-arachnoid hemorrhage in a subject, comprising:
    providing a sample of plasma, serum or cerebrospinal fluid from the subject;
    providing a control sample;
    analyzing the sample from the subject and detecting a level of expression of glutathione S transferase P and a polypeptide selected from the group consisting of peroxiredoxin 1, peroxiredoxin 2, peroxiredoxin 5 and peroxiredoxin 6 and variants or mutants thereof in the plasma, serum or cerebrospinal fluid sample taken from the subject, wherein the variants or mutants have a homology of at least 90% with the polypeptide, comprising:
        assaying the sample using an anti-human GST-P antibody and an antibody that recognizes, binds to or has affinity for a polypeptide selected from the group consisting of peroxiredoxin 1, peroxiredoxin 2, peroxiredoxin 5 and peroxiredoxin 6 and mutants or variants thereof in the sample or the control sample, wherein the variants or mutants have a homology of at least 90% with the polypeptide; and
    diagnosing the subject as having the brain damage-related disorder based on an increased level of expression of the glutathione S transferase P and the polypeptide in the sample from the subject as compared to the control sample.

6. A method of diagnosing a brain damage-related disorder selected from stroke and sub-arachnoid hemorrhage in a subject, comprising:

assaying a plasma, serum or cerebrospinal fluid sample taken from the subject using a GST-P antibody having a label, wherein the GST-P antibody recognizes, binds to or has affinity for glutathione S transferase P in the plasma, serum or cerebrospinal fluid sample taken from the subject;

assaying the plasma, serum or cerebrospinal fluid sample taken from the subject using an antibody having an enzymatic or fluorescent label, wherein the antibody recognizes, binds to, or has affinity for a polypeptide selected from the group consisting of peroxiredoxin 1, peroxiredoxin 2, peroxiredoxin 5 and peroxiredoxin 6 and mutants or variants thereof in the plasma, serum or cerebrospinal fluid sample taken from the subject, wherein the variants or mutants have a homology of at least 90% with the polypeptide;

detecting glutathione S transferase P and the polypeptide;

assaying a control sample of plasma, serum or cerebrospinal fluid with the antibody; and diagnosing the subject as having the brain damage-related disorder based on an increased binding of the antibody to the polypeptide in the sample from the subject as compared with binding of the antibody in the control sample.

7. The method of claim 6, wherein the GST-P antibody is an anti-human GST-P antibody and wherein the antibody that recognizes, binds to or has affinity for Peroxiredoxin 1, peroxiredoxin 2, peroxiredoxin 5, and peroxiredoxin 6 is selected from the group consisting of an anti-human peroxiredoxin 1 antibody, an anti-human peroxiredoxin 2 antibody, an anti-human peroxiredoxin 5 antibody, and an anti-human peroxiredoxin 6 antibody, where each antibody comprises a full antibody or a functional fragment of the antibody selected from the group consisting of Fab, FAB2 and SCFv, and wherein each antibody is a labelled antibody.

8. The method of claim 6, wherein assaying comprises a chemiluminescent assay and wherein each antibody is labeled with horseradish peroxidase.

\* \* \* \* \*